United States Patent
Ichihashi et al.

(10) Patent No.: US 12,315,162 B2
(45) Date of Patent: May 27, 2025

(54) IMAGE ANALYZER, CELL CULTURE OBSERVATION DEVICE, IMAGE ANALYSIS METHOD, PROGRAM, AND DATA PROCESSING SYSTEM

(71) Applicant: NIKON CORPORATION, Tokyo (JP)

(72) Inventors: Toru Ichihashi, Yokohama (JP); Yoichi Yamazaki, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 536 days.

(21) Appl. No.: 17/639,855

(22) PCT Filed: Sep. 4, 2020

(86) PCT No.: PCT/JP2020/033666
§ 371 (c)(1),
(2) Date: Jun. 22, 2022

(87) PCT Pub. No.: WO2021/045214
PCT Pub. Date: Mar. 11, 2021

(65) Prior Publication Data
US 2022/0327694 A1   Oct. 13, 2022

(30) Foreign Application Priority Data

Sep. 4, 2019 (JP) .................................. 2019-161011

(51) Int. Cl.
*G06T 7/00* (2017.01)
*G01N 21/17* (2006.01)
(Continued)

(52) U.S. Cl.
CPC ............ *G06T 7/0016* (2013.01); *G01N 21/17* (2013.01); *G01N 33/4833* (2013.01); *G06T 5/70* (2024.01);
(Continued)

(58) Field of Classification Search
CPC ....... G06T 5/70; G06T 7/0012; G06T 7/0016; G06T 7/62; G06T 2207/10056;
(Continued)

(56) References Cited

U.S. PATENT DOCUMENTS 10,114,003 B2 * 10/2018 Tsujimoto .............. C12M 41/36
2011/0002525 A1   1/2011 Mimura et al.
(Continued)

FOREIGN PATENT DOCUMENTS

JP   2009-207416 A   9/2009
JP   2009-229276 A   10/2009
(Continued)

OTHER PUBLICATIONS

Bobadilla, Ana Victoria Ponce, et al. "In vitro cell migration quantification method for scratch assays." Journal of the Royal Society Interface 16.151 (2019): 20180709. (Year: 2019).*

(Continued)

*Primary Examiner* — Scott A Rogers
(74) *Attorney, Agent, or Firm* — Oliff PLC

(57) ABSTRACT

An image analyzer including: an area setting unit configured to extract a scratch area that is an area having no cells from a reference image selected from a plurality of images acquired by imaging cells in a time series and set a reference region corresponding to the scratch area in the plurality of (Continued)

images; a calculation unit configured to calculate an area of a cell region within the reference region and/or the ratio of an area of the cell region to the reference region from the plurality of images; and a control unit configured to cause a display device to display a change in a time series of the calculated area of the cell region and/or the ratio of the area of the cell region to the reference region.

12 Claims, 17 Drawing Sheets

(51) Int. Cl.
    *G01N 33/483*     (2006.01)
    *G06T 5/70*     (2024.01)
    *G06T 7/62*     (2017.01)

(52) U.S. Cl.
    CPC ...... *G06T 7/62* (2017.01); *G06T 2207/10056* (2013.01); *G06T 2207/30024* (2013.01)

(58) Field of Classification Search
    CPC .......... G06T 2207/30024; G01N 21/17; G01N 33/4833; C12M 41/36
    See application file for complete search history.

(56) References Cited

U.S. PATENT DOCUMENTS

| | | |
|---|---|---|
| 2011/0013821 A1 | 1/2011 | Mimura et al. |
| 2012/0028288 A1 | 2/2012 | Nitta |
| 2013/0051651 A1 | 2/2013 | Leary et al. |
| 2014/0226069 A1 | 8/2014 | Oshima et al. |
| 2017/0335404 A1 | 11/2017 | Skubitz et al. |
| 2022/0114819 A1* | 4/2022 | Ichihashi ................ G06T 7/246 |
| 2023/0127415 A1* | 4/2023 | Nagase ................ G06V 20/698 |
| | | 382/133 |

FOREIGN PATENT DOCUMENTS

| | | |
|---|---|---|
| JP | 2014-075999 A | 5/2014 |
| JP | 2014-150734 A | 8/2014 |
| JP | 2014-179061 A | 9/2014 |
| JP | 7011770 B2 * | 1/2022 |
| WO | 2007/066684 A1 | 6/2007 |

OTHER PUBLICATIONS

Liang, Chun-Chi, Ann Y. Park, and Jun-Lin Guan. "In vitro scratch assay: a convenient and inexpensive method for analysis of cell migration in vitro." Nature protocols 2.2 (2007): 329-333. (Year: 2007).*
Jul. 18, 2023 Office Action issued in Japanese Patent Application No. 2019-161011.
Bettenworth et al., "Quantitative Stain-Free and Continuous Multimodal Monitoring of Wound Healing In Vitro with Digital Holographic Microscopy," Plos One, vol. 9, No. 9, Sep. 24, 2014, pp. 1-10.
Sep. 11, 2023 Extended Search Report issued in European Patent Application No. 20860461.1.
Nov. 10, 2020 Written Opinion of the International Searching Authority issued in Patent Application No. PCT/JP2020/033666.
Nov. 10, 2020 International Search Report issued in Patent Application No. PCT/JP2020/033666.
Jan. 9, 2024 Office Action issued in Japanese Patent Application No. 2019-161011.

* cited by examiner

IMAGE ANALYZER, CELL CULTURE OBSERVATION DEVICE, IMAGE ANALYSIS METHOD, PROGRAM, AND DATA PROCESSING SYSTEM

TECHNICAL FIELD

The present invention relates to an image analyzer, a cell culture observation device, an image analysis method, a program, and a data processing system.

Priority is claimed on Japanese Patent Application No. 2019-161011, filed Sep. 4, 2019, the content of which is incorporated herein by reference.

BACKGROUND ART

The migration ability of cells deeply relates to various diseases. Therefore, there is demand for quantitative evaluation of the migration ability of cells. As an analysis method for evaluating the migration ability of cells, scratch assay is known. In addition, for example, a device that determines a disease accompanying a migration disability by evaluating the migration ability of neuro cells of the brain based on an image analysis is known (Patent Literature 1).

CITATION LIST

Patent Literature

[Patent Literature 1]
Japanese Unexamined Patent Application, First Publication No. 2014-150734

SUMMARY OF INVENTION

One aspect of the present invention is an image analyzer including: an area setting unit configured to extract a scratch area that is an area having no cells from a reference image selected from a plurality of images acquired by imaging cells in a time series and set a reference region corresponding to the scratch area in the plurality of images; a calculation unit configured to calculate an area of a cell region within the reference region and/or the ratio of an area of the cell region to the reference region from the plurality of images; and a control unit configured to cause a display device to display a change in a time series of the calculated area of the cell region and/or the ratio of the area of the cell region to the reference region.

Another aspect of the present invention is a cell culture observation device including: the image analyzer described above; a culture device configured to culture the cells housed in a culture container; and a microscope configured to capture the plurality of images.

Another aspect of the present invention is an image analysis method including: an area setting step of extracting a scratch area that is an area having no cells from a reference image selected from a plurality of images acquired by imaging cells in a time series and setting a reference region corresponding to the scratch area in the plurality of images; a calculation step of calculating an area of a cell region within the reference region and/or the ratio of an area of the cell region to the reference region from the plurality of images; and a control step of causing a display device to display a change in a time series of the calculated area of the cell region and/or the ratio of the area of the cell region to the reference region.

Another aspect of the present invention is a program causing a computer to execute: an area setting step of extracting a scratch area that is an area having no cells from a reference image selected from a plurality of images acquired by imaging cells in a time series and setting a reference region corresponding to the scratch area in the plurality of images; a calculation step of calculating an area of a cell region within the reference region and/or the ratio of an area of the cell region to the reference region from the plurality of images; and a control step of causing a display device to display a change in a time series of the calculated area of the cell region and/or the ratio of the area of the cell region to the reference region.

Another aspect of the present invention is a data processing system that outputs analysis information to a terminal of a user using cloud computing, the data processing system including a server, the server including: an acquisition unit configured to acquire a plurality of images acquired by imaging cells in a time series through a network; an area setting unit configured to extract a scratch area that is an area having no cells from a reference image selected from a plurality of images acquired by imaging cells in a time series and set a reference region corresponding to the scratch area in the plurality of images; a calculation unit configured to calculate an area of a cell region within the reference region and/or the ratio of an area of the cell region to the reference region from the plurality of images; and a control unit configured to output a change in a time series of the calculated area of the cell region and/or the ratio of the area of the cell region to the reference region to the terminal of the user as the analysis information.

Another aspect of the present invention is an image analyzer including: a storage unit configured to store a program executed by the image analyzer; and a control unit configured to control an operation of the image analyzer by executing the program, in which, the control unit controls operations of selecting a reference image from a plurality of images acquired by imaging cells in a time series, extracting an area having no cells in the reference image as a scratch area; sets a reference region corresponding to the scratch area in each of the plurality of images, and setting a predetermined color for the cell region positioned within the reference region of each of the plurality of images and outputting a change in the time series of the cell region to a display device.

DESCRIPTION OF EMBODIMENTS

First Embodiment

Figure 1:
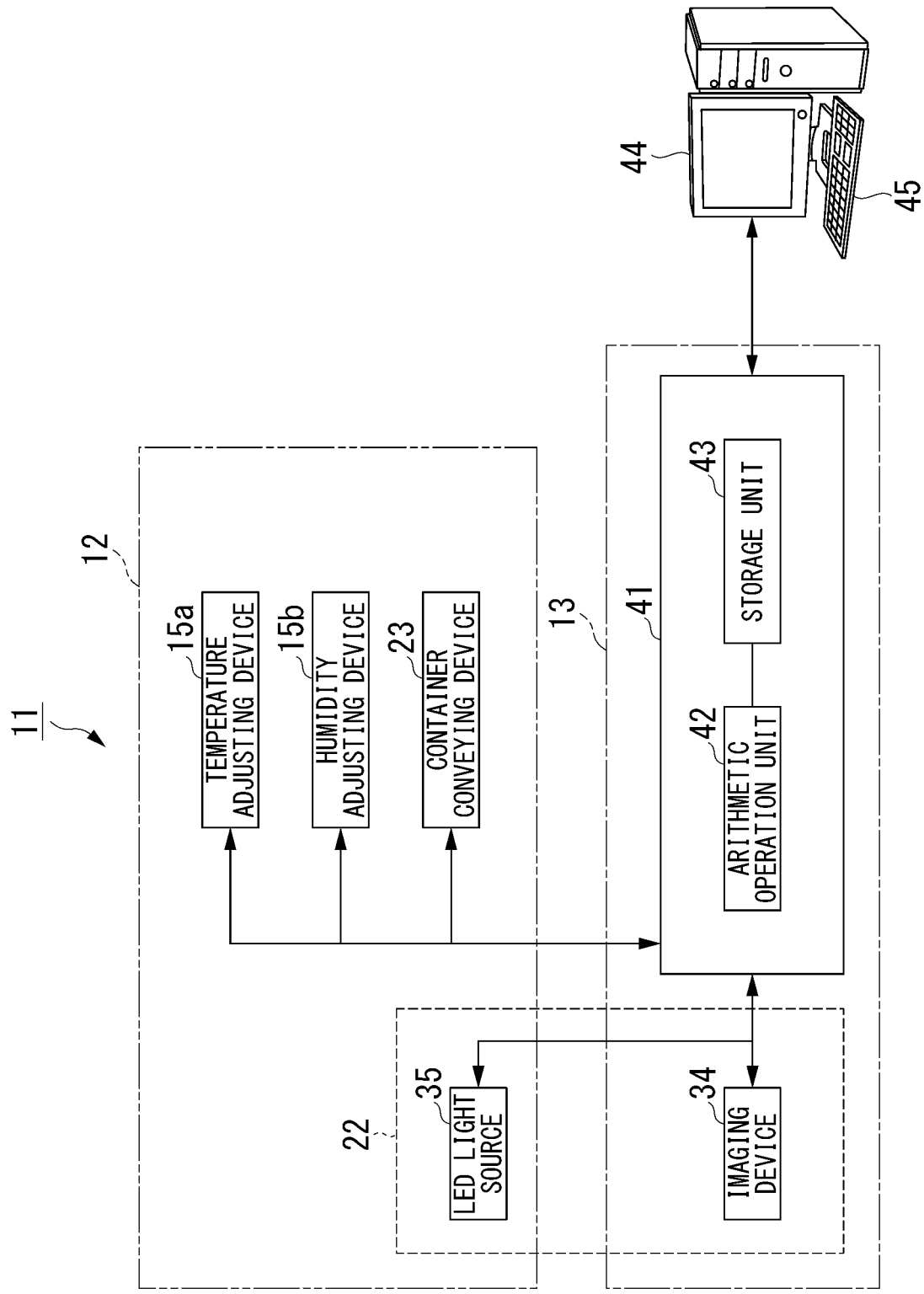
FIG. 1 is a block diagram illustrating an overview of an incubator including an image analyzer according to a first embodiment.
Figure 2:
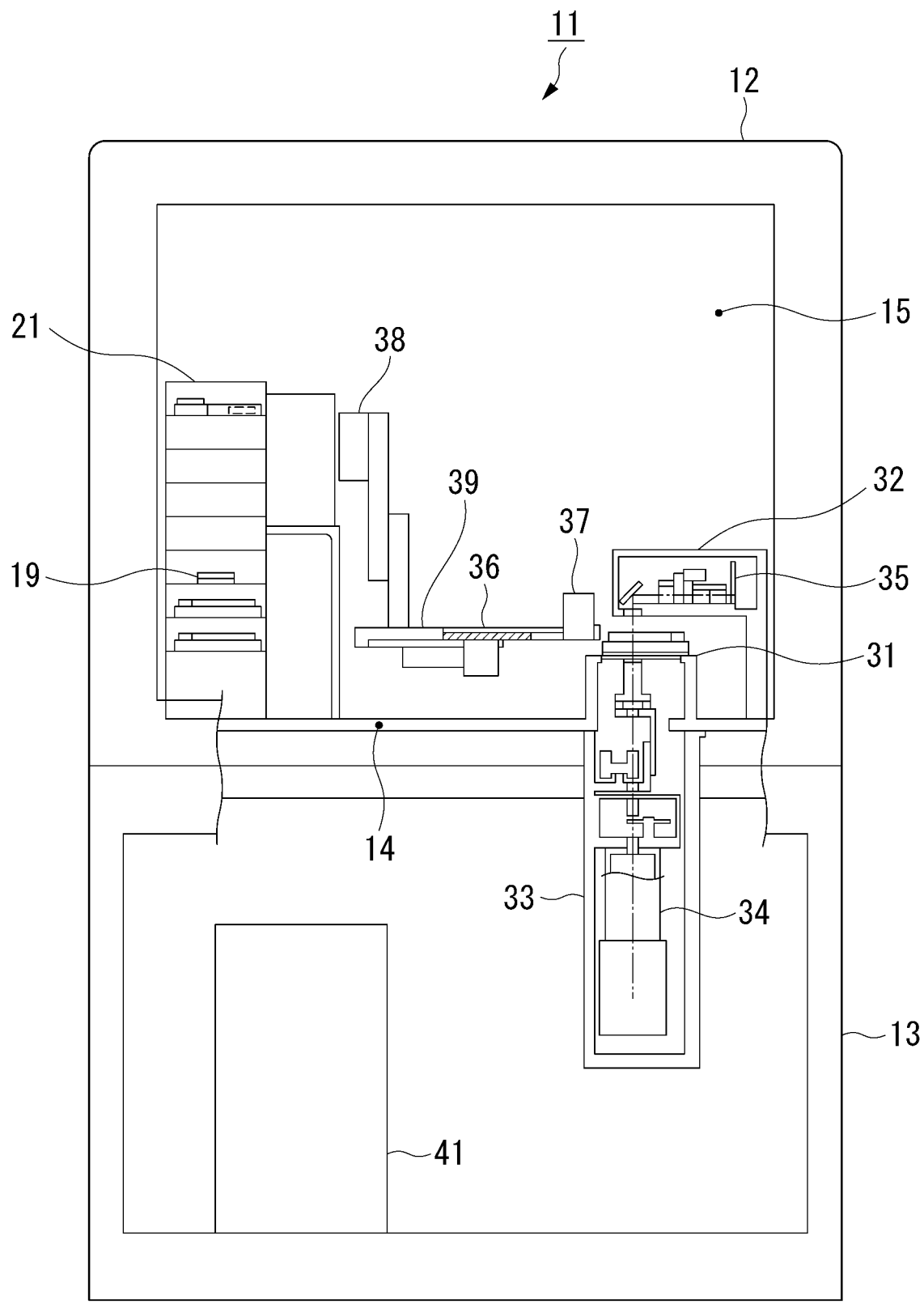
FIG. 2 is a diagram illustrating an example of a front view of the incubator according to the first embodiment.
Figure 3:
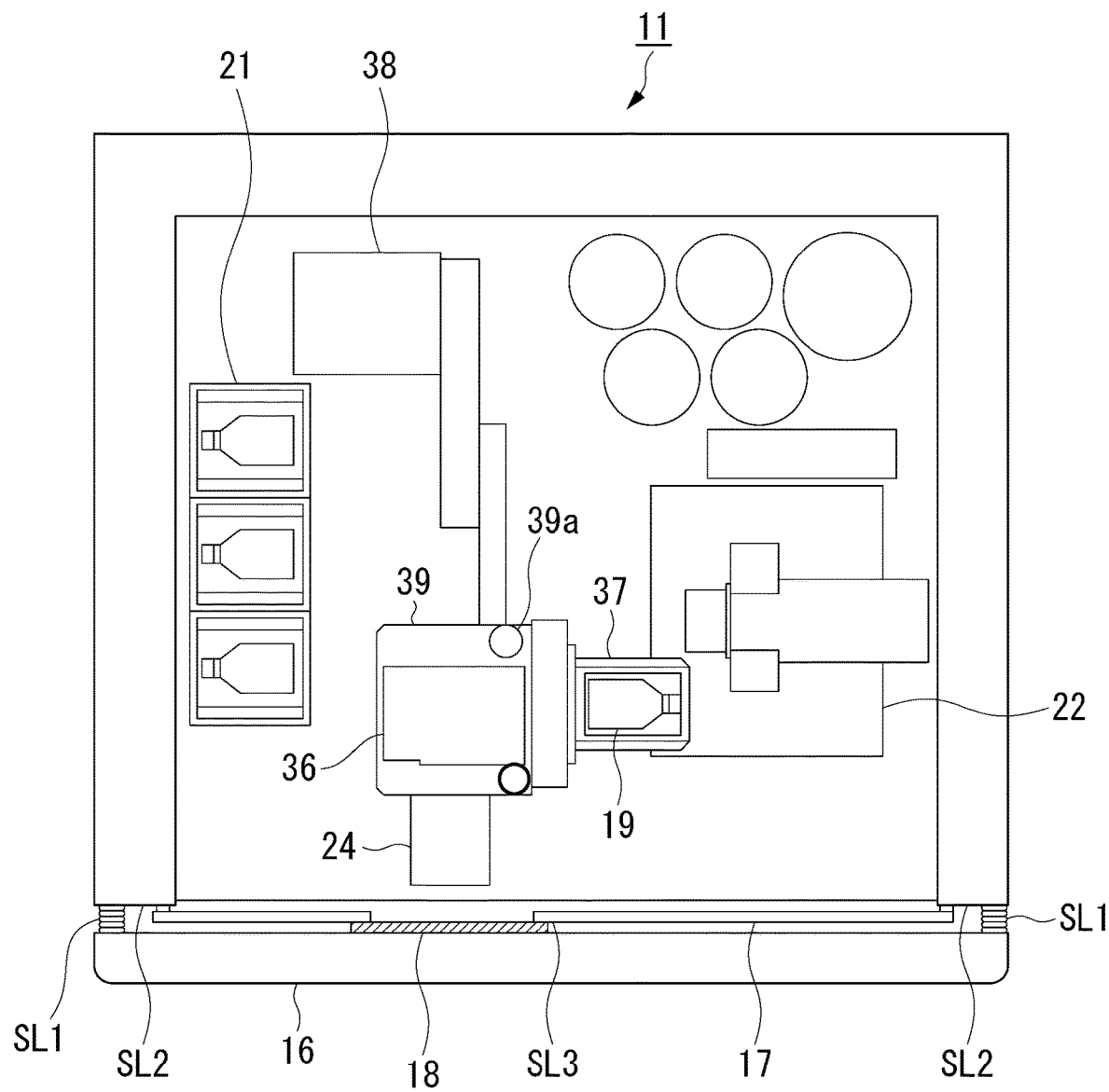
FIG. 3 is a diagram illustrating an example of a plan view of the incubator according to the first embodiment.

Hereinafter, a first embodiment will be described with reference to the drawings. FIG. 1 is a block diagram illustrating an overview of an incubator 11 including an image analyzer according to an embodiment. FIGS. 2 and 3 are diagrams illustrating examples of a front view and a plan view of the incubator 11 according to this embodiment.

This incubator 11 is an example of a cell culture observation device.

The incubator 11 according to the embodiment has an upper casing 12 and a lower casing 13. The upper casing 12 is placed on the lower casing 13 in an assembled state of the incubator 11. In addition, an internal space of the upper casing 12 and the lower casing 13 is divided vertically using a base plate 14.

First, an overview of the upper casing 12 will be described. Inside the upper casing 12, a thermostatic chamber 15 that cultures cells is formed. This thermostatic chamber 15 includes a temperature adjusting device 15a and a humidity adjusting device 15b, and the inside of the thermostatic chamber 15 is maintained to be in an environment that is appropriate for culture of cells (for example, an atmosphere of a temperature of 37° C. and a humidity of 90%) (in addition, illustration of the temperature adjusting device 15a and the humidity adjusting device 15b is omitted in FIGS. 2 and 3). In other words, the inside of the thermostatic chamber 15 can be maintained at predetermined environment conditions.

A front face of the thermostatic chamber 15, a large door 16, an intermediate door 17, and a small door 18 are disposed. The large door 16 covers front faces of the upper casing 12 and the lower casing 13. The intermediate door 17 covers the front face of the upper casing 12 and separates environments of the thermostatic chamber 15 from the outside when the large door 16 is opened. The small door 18 is a door used for carrying in and out a culture container 19 that cultures cells and is attached to the intermediate door 17. By carrying in and out the culture container 19 from this small door 18, an environmental change of the thermostatic chamber 15 can be inhibited. In addition, the airtightness of the large door 16, the airtightness of the intermediate door 17, and the airtightness of the small door 18 are respectively maintained using a packing SL1, a packing SL2, and a packing SL3. For example, the culture container 19 is a well plate (for example, a plate having six wells or the like).

In addition, in the thermostatic chamber 15, a stocker 21, an observation unit 22, a container conveying device 23, and a conveyance base 24 are disposed. Here, the conveyance base 24 is disposed in front of the small door 18 and allows the culture container 19 to be carried in and out through the small door 18.

The stocker 21 is disposed on the left side of the thermostatic chamber 15 when seen from the front face of the upper casing 12 (a lower side in FIG. 3 and a door side of the large door 16 and the like). The stocker 21 has a plurality of shelves, and a plurality of culture containers 19 can be housed in each of the shelves of the stocker 21. In addition, in each culture container 19, cells that are targets for culture are housed together with a culture medium. In this way, the thermostatic chamber 15 houses the culture containers 19 that culture cells. The thermostatic chamber 15 is one example of a culture device that cultures cells housed in the culture containers 19.

The observation unit 22 is disposed on the right side of the thermostatic chamber 15 when seen from the front face of the upper casing 12 (a lower side in FIG. 3 and the door side of the large door 16 and the like). This observation unit 22 can perform time lapse observation of cells inside the culture container 19. Here, the time lapse observation is a technique for observing a change in a time series of a sample based on a plurality of captured images (time lapse images) by imaging the sample (for example, a cell) at each of predetermined times based on an imaging schedule set in advance. The imaging of a sample may be performed at constant time intervals or at different time intervals.

Here, the observation unit 22 is fitted into and disposed in an opening part of the base plate 14 of the upper casing 12. The observation unit 22 has a sample stand 31, a stand arm 32 extending to a side above the sample stand 31, a microscopic optical system for observation of a phase difference, and a main body part 33 in which an imaging device 34 is built. While the sample stand 31 and the stand arm 32 are disposed in the thermostatic chamber 15, the main body part 33 is housed inside the lower casing 13.

The sample stand 31 is composed of a translucent material, and the culture container 19 can be placed thereon. This sample stand 31 is configured to be able to move in a horizontal direction and can adjust a position of the culture container 19 displaced on an upper face thereof. In addition, a LED light source 35 is built into the stand arm 32. According to transmitting illumination of the cells of the culture container 19 from above the sample stand 31 using the stand arm 32, the imaging device 34 can acquire a microscopic image of the cells using the microscopic optical system. The imaging device 34 images cells housed in the culture container inside the thermostatic chamber 15 at each of predetermined times.

In the following description, image data (a plurality of images) of a time series that is acquired by performing time-lapse observation of cells will be referred to as a time lapse image TP. A plurality of images in which cells are captured are included in the time lapse image TP. The observation unit 22 is one example of a microscope capturing a time lapse image TP.

As described above, in this embodiment, the microscopic optical system of the observation unit 22 allows observation of cells of the culture container 19, for example, using phase difference observation. In other words, the microscopic optical system of the observation unit 22 is a phase contrast microscope. Thus, a time lapse image TP acquired using time lapse observation according to this embodiment is a phase contrast image.

In addition, the time lapse image TP is not limited to a phase contrast image. For example, the time lapse image TP may be a differential interference image in a case in which the microscopic optical system of the observation unit 22 is a differential interference microscope and may be a fluorescence image in a case in which the microscopic optical system of the observation unit 22 is a fluorescence microscope.

The container conveying device 23 is disposed at the center of the thermostatic chamber 15 when seen from the front face of the upper casing 12. This container conveying device 23 exchanges the culture container 19 between the stocker 21, the sample stand 31 of the observation unit 22, and the conveyance base 24.

As illustrated in FIG. 3, the container conveying device 23 includes a vertical robot 38 having an articulated arm, a rotation stage 39, a mini stage 36, and an arm part 37. The rotation stage 39 is attached to a tip end part of the vertical robot 38 such that it can rotate in a horizontal direction by 180° through a rotation shaft 35a. For this reason, the rotation stage 39 can cause the arm part 37 to face the stocker 21, the sample stand 31, and the conveyance base 24, respectively.

In addition, the mini stage 36 is attached to the rotation stage 39 such that it can slide in the horizontal direction with respect to the rotation stage 39. The arm part 37 gripping the culture container 19 is attached to the mini stage 36.

Next, an overview of the configuration of the lower casing 13 illustrated in FIG. 2 will be described. Inside the lower casing 13, the main body part 33 of the observation unit 22 and a control device 41 of the incubator 11 are housed.

As illustrated in FIG. 1, the control device 41 is connected to the temperature adjusting device 15a, the humidity adjusting device 15b, the observation unit 22, and the container conveying device 23, respectively. This control device 41 includes an arithmetic operation unit (processor) 42 and a storage unit 43 and integrally controls each unit of the incubator 11 in accordance with a predetermined program.

For example, the control device 41 maintains the inside of the thermostatic chamber 15 at predetermined environment conditions by controlling the temperature adjusting device 15a and the humidity adjusting device 15b, respectively. In addition, the control device 41 controls the observation unit 22 and the container conveying device 23 based on a predetermined observation schedule, thereby automatically performing an observation sequence of the culture container 19.

Furthermore, the control device 41 causes the arithmetic operation unit 42 to perform an image analysis of a time lapse image TP captured by the imaging device 34. In the image analysis performed by this arithmetic operation unit 42, for example, a process of setting a scratch area formed in a culture area of cells as a reference region RS from the reference image PS of the time lapse image TP and calculating an area of each cell region of cells inside the set reference region from the time lapse image TP is included. The arithmetic operation unit 42 is one example of the image analyzer.

Figure 4:
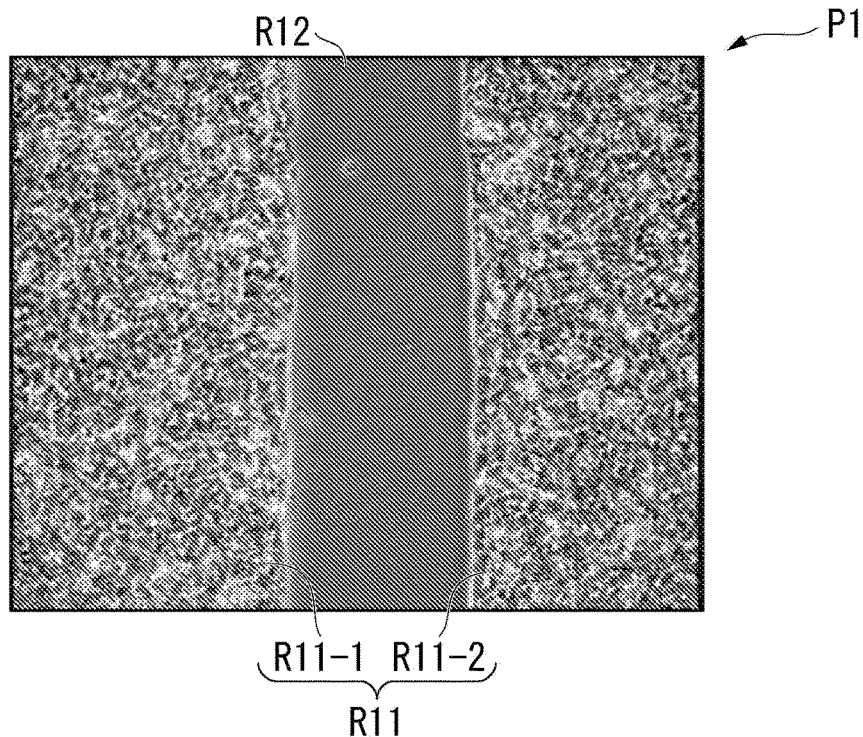
FIG. 4 is a diagram illustrating an example of a scratch area according to the first embodiment.

Here, a scratch area will be described with reference to FIG. 4. FIG. 4 is a diagram illustrating an example of a scratch area according to this embodiment. FIG. 4 illustrates an image P1 as one example of an image P included in a time lapse image TP. In the image P1, a culture area R11 is illustrated as a culture area of cells. The culture area R11 is formed from a culture area R11-1 and a culture area R11-2, and a scratch area R12 is formed between the culture area R11-1 and the culture area R11-2.

A scratch area, for example, is an area having no cells formed by scratching a culture area of cells in the culture container 19 using a bar-shaped member or the like in a 100-percent confluent state. In other words, a scratch area is a gap formed in a culture area. The scratch area may be also regarded as a wound pattern formed by scratching a culture area of cells.

Here, the scratch area is formed by an observer (for example, a user) scratching a culture area of cells, for example, using a pipette tip or the like. Although the shape of a scratch area is not particularly limited, in this embodiment, as an example, the shape of a scratch area is in the form of a belt shape like a scratch area R12 illustrated in FIG. 4.

In accordance with migration and propagation of cells, the cells gradually fill a scratch area in accordance with elapse of time. A scratch area filled with cells is also called a scratch area being infiltrated by the cells.

Next, the description of the incubator 11 will be continued with reference back to FIG. 1.

In time lapse observation, the imaging device 34 performs imaging such that a position of the scratch area described above is a common position in the time lapse image TP. The imaging device 34, for example, performs positioning with a marker (alignment mark) of a well plate that is a culture container. In a case in which the position of the scratch area deviates from an initial position, the imaging device 34 corrects the position by moving the sample stand 31 in the horizontal direction using the control device 41.

A display unit 44 displays information that includes various images. For example, the display unit 44 displays a result of an image analysis process using the arithmetic operation unit 42. The display unit 44 includes a display.

An operation unit 45 includes a touch panel, a mouse, a keyboard, or the like. In addition, in a case in which the operation unit 45 is a touch panel, the operation unit 45 and the display unit 44 may be integrally configured. Furthermore, the operation unit 45 and the display unit 44 may be configured as a touch panel provided in the upper casing 12 or the lower casing 13.

In addition, an observer sets environment conditions of the thermostatic chamber 15 by operating this operation unit 45.

[Example of Observation Operation]

Next, one example of an observation operation in the incubator 11 will be described with reference to a flowchart illustrated in FIG. 5.

Figure 5:
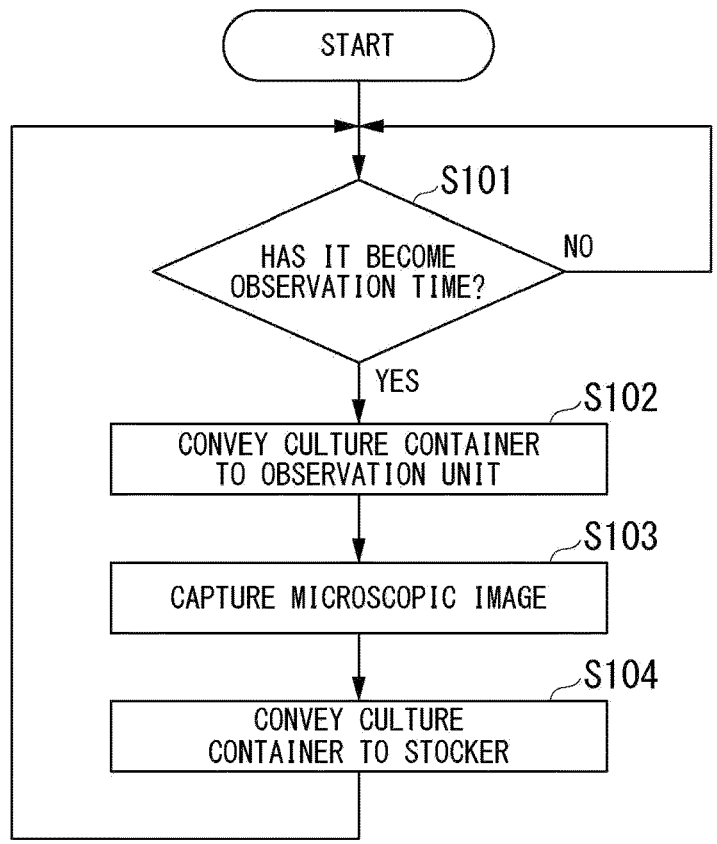
FIG. 5 is a diagram illustrating an example of an observation operation in the incubator according to the first embodiment.

FIG. 5 is a diagram illustrating an example of an observation operation in the incubator 11 according to this embodiment. This drawing illustrates an operation example of performing time lapse observation of the culture container 19 carried inside the thermostatic chamber 15 in accordance with a registered observation schedule. Here, in each well of the culture container 19, a scratch area is formed in advance in a culture area of cells of the well by an observer. In the following description, a technique of performing an analysis by observing cells in the culture container 19 in which a scratch area is formed will be also referred to a scratch assay.

Step S101: The arithmetic operation unit 42 compares the observation schedule of management data of the storage unit 43 with the current date and time and determines whether or not an observation start time of the culture container 19 that is an observation target has arrived. In a case in which the observation start time has arrived (Step S101: Yes), the arithmetic operation unit 42 causes the process to proceed to S102. On the other hand, in a case in which the observation time of the culture container 19 has not arrived (Step S101: No), the arithmetic operation unit 42 stands by until a time of the next observation schedule.

Step S102: The arithmetic operation unit 42 instructs the container conveying device 23 to convey the culture container 19 that is an observation target corresponding to the observation schedule. Then, the container conveying device 23 carries out the instructed culture container 19 from the stocker 21 and places the culture container 19 on the sample stand 31 of the observation unit 22. In addition, in the step in which the culture container 19 is placed on the sample stand 31, an observation image of the entire culture container 19 is captured by a bird's view camera (not illustrated) built into the stand arm 32.

Step S103: The arithmetic operation unit 42 instructs the observation unit 22 to capture a microscopic image (for example, a phase contrast image) of cells. The observation unit 22 lights the culture container 19 by turning on the LED light source 35 and captures a microscopic image of cells of the inside of the culture container 19 by driving the imaging device 34.

At this time, the imaging device 34 captures a microscopic image based on imaging conditions (a magnification of an objective lens and an observation site inside the container) designated by an observer based on the management data stored in the storage unit 43. For example, in a case in which a plurality of points inside the culture container 19 are observed, the observation unit 22 sequentially adjusts positions of the culture container 19 by driving the sample stand 31 and captures microscopic images at each of the points. In addition, data of the microscopic images acquired in S103 is read by the control device 41 and is recorded in the storage unit 43 in accordance with control of the arithmetic operation unit 42.

Step: S104: The arithmetic operation unit 42 instructs the container conveying device 23 to convey the culture container 19 after an end of the observation schedule. Then, the container conveying device 23 conveys the instructed culture container 19 from the sample stand 31 of the observation unit 22 to a predetermined housing position in the stocker 21. Thereafter, the arithmetic operation unit 42 ends the observation sequence and returns the process to S101.

In accordance with the sequence described above, image data of a time series observed using the incubator 11 is stored in the storage unit 43 as a time lapse image TP. In the following description, acquisition of a time lapse image TP may be also referred to as time lapse imaging.

[Image Analysis Process]

Next, the configuration of the arithmetic operation unit 42 and an image analysis process performed by the arithmetic operation unit 42 will be described with reference to FIGS. 6 to 9.

Figure 6:
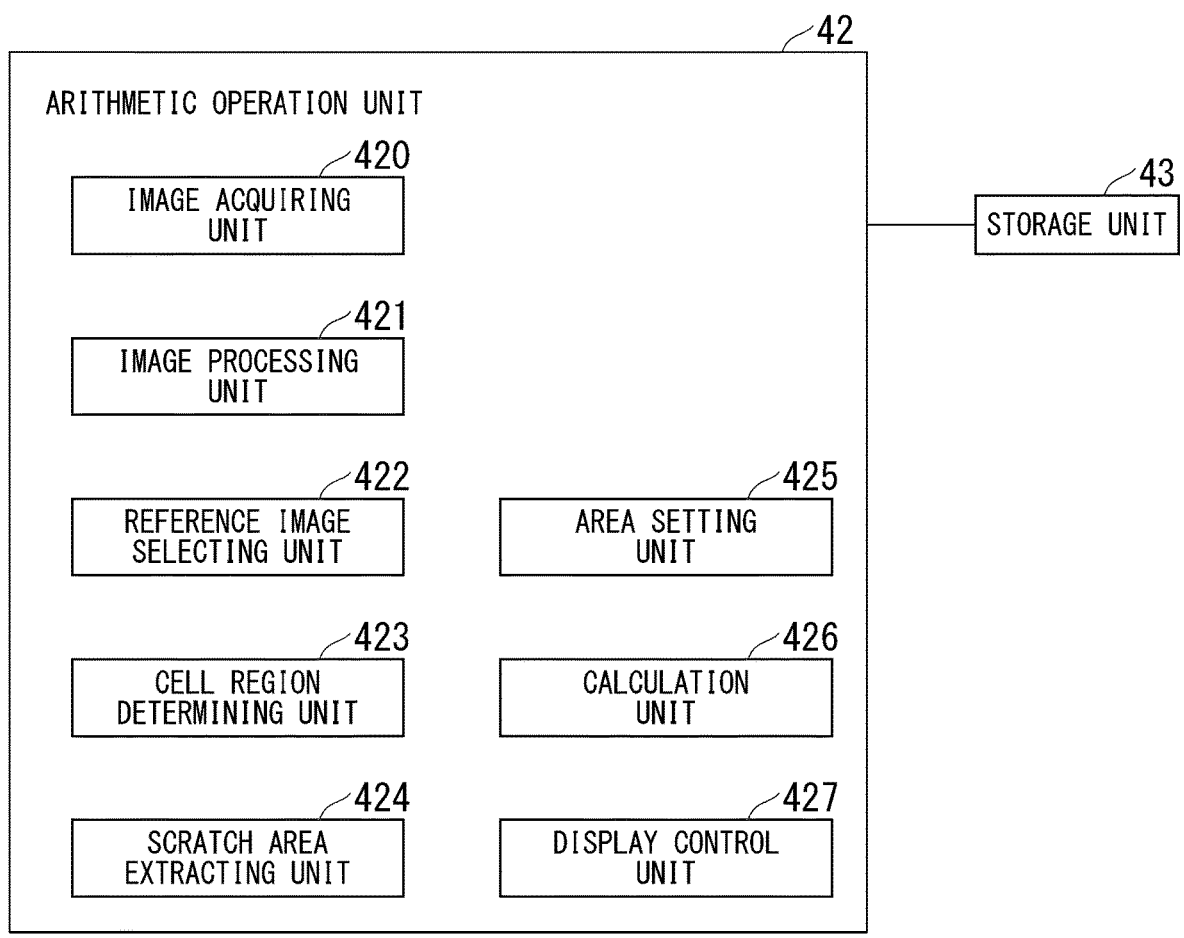
FIG. 6 is a diagram illustrating an example of the functional configuration of an arithmetic operation unit according to the first embodiment.

FIG. 6 is a diagram illustrating an example of the functional configuration of the arithmetic operation unit 42 according to this embodiment. The arithmetic operation unit 42 includes an image acquiring unit (acquisition unit) 420, an image processing unit 421, a reference image selecting unit 422, a cell region determining unit 423, a scratch area extracting unit 424, an area setting unit 425, a calculation unit 426, and a display control unit (control unit) 427.

The arithmetic operation unit 42, for example, is realized using a central processing unit (CPU), and each of the image acquiring unit 420, the image processing unit 421, the reference image selecting unit 422, the cell region determining unit 423, the scratch area extracting unit 424, the area setting unit 425, the calculation unit 426, and the display control unit 427 is realized by the CPU reading a program from a read only memory (ROM) and executing a process.

The image acquiring unit 420 acquires a time lapse image TP captured by the imaging device 34. Here, the image acquiring unit 420 acquires the time lapse image TP from the storage unit 43.

The image processing unit 421 performs various image processes (for example, a noise eliminating process and the like) on the time lapse image TP.

The reference image selecting unit 422 selects a predetermined reference image PS from the time lapse image TP and stores the reference image PS in the storage unit 43. Here, the reference image PS is an image used for setting a scratch area among images P included in the time lapse image TP.

In addition, although the selection of the reference image PS will be described below, the selection may be automatic selection using the reference image selecting unit 422 or selection performed by an observer.

The cell region determining unit 423 determines a cell region of cells in an image P included in the time lapse image TP. A cell region is an area in which cells are imaged in an image P included in the time lapse image TP. In a cell region, an image of a cell group formed from a plurality of cells or an image of one cell is included.

The scratch area extracting unit 424 extracts a scratch area from the reference image PS.

The area setting unit 425 sets the scratch area from the reference image PS as a reference region RS and stores the reference region RS in the storage unit 43. The reference region RS is an area that becomes a reference for calculating an area of a cell region within the scratch area.

The calculation unit 426 calculates an area of cell region of cells within the reference region RS from each of the time lapse image TP. Then, the calculation unit 426 stores the calculated area (analysis information) of the cell region of cells within the reference region RS in the storage unit 43 in association with each image of the time lapse image TP used for the calculation.

The display control unit 427 controls screen display of the display unit 44. Here, for example, the display control unit 427 outputs a change in a time series of the area of the cell region calculated by the calculation unit 426 to the display unit 44 as analysis information (analysis data) and causes the display unit to display the change.

Figure 7:
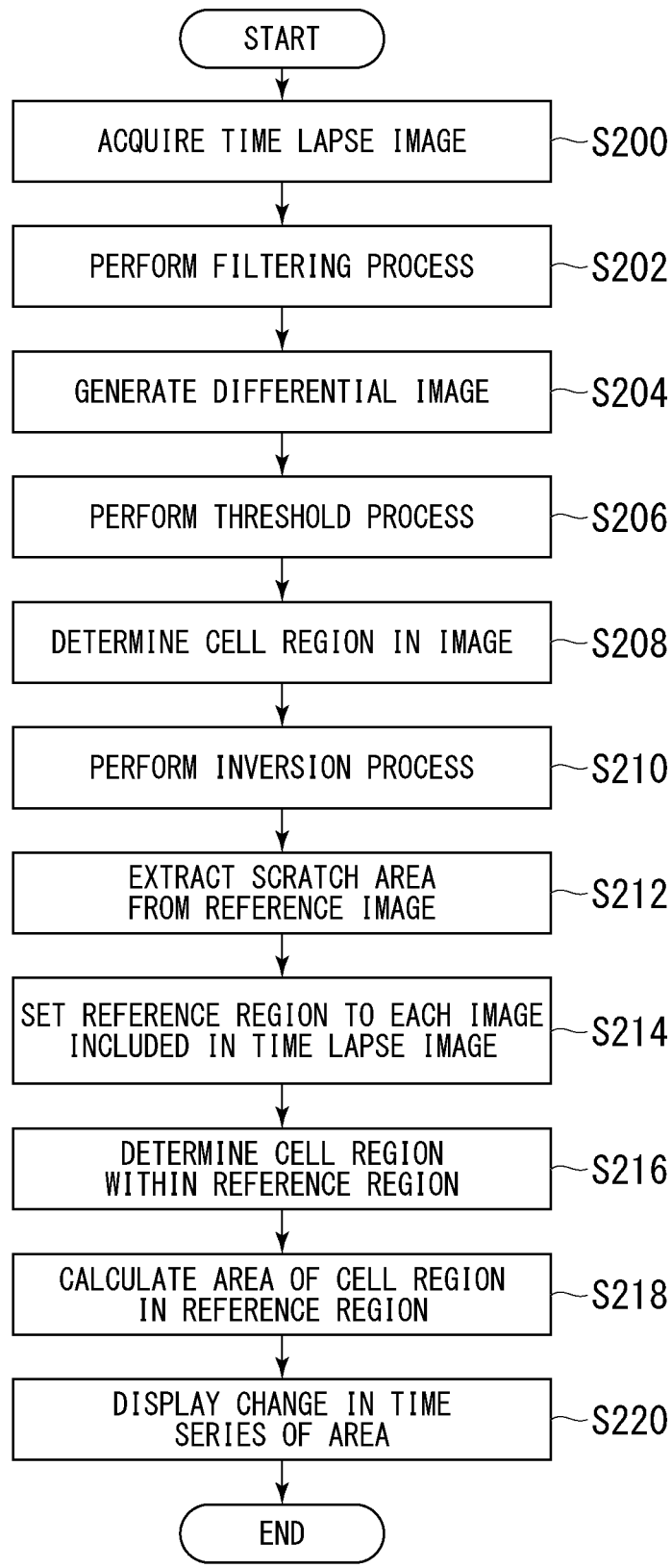
FIG. 7 is a diagram illustrating an example of an image analysis process according to the first embodiment.

Next, an image analysis process of the arithmetic operation unit 42 will be described with reference to FIG. 7. FIG. 7 is a diagram illustrating an example of the image analysis process according to this embodiment. The image analysis process illustrated in FIG. 7 is performed after the observation operation is performed (for example, after the observation operation, during the observation operation, or the like) by the incubator 11 in accordance with the observation schedule described with reference to FIG. 5 as one example.

Step S200: The image acquiring unit 420 acquires a time lapse image TP of the culture container 19 including a scratch area imaged by the imaging device 34. Here, the image acquiring unit 420 acquires a time lapse image TP from the storage unit 43. The image acquiring unit 420 supplies the acquired time lapse image TP to the reference image selecting unit 422.

In this embodiment, the time lapse image TP acquired by the image acquiring unit 420, for example, is a plurality of images captured for each observation time indicated by the observation schedule. For example, the image acquiring unit 420 acquires the time lapse image TP at one time after observation ends. In addition, the image acquiring unit 420 may acquire an image that is captured each time an image of cells is captured at an observation time indicated by the observation schedule as a time lapse image TP.

Furthermore, the image acquiring unit 420 may directly acquire a time lapse image TP from the imaging device 34 instead of the storage unit 43.

Step S202: The image processing unit 421 performs a filtering process on the time lapse image TP acquired by the image acquiring unit 420. The image processing unit 421 blurs the time lapse image TP using the filtering process, thereby decreasing an amount of a local luminance change included in the time lapse image TP.

The image processing unit 421 performs the filtering process, for example, using a mean filter. In the mean filter, a mean value of luminance values of pixels that are processing targets and luminance values of pixels disposed in the vicinity thereof is set as a luminance value of the pixels that is the processing target. Here, pixels that are processing targets are all the pixels included in an image, Step S204: The image processing unit 421 generates a differential image. Here, the image processing unit 421 calculates absolute values of differences between pixel values of pixels of an image P included in a time lapse image TP acquired by the image acquiring unit 420 and an image acquired by performing the filtering process on this image as pixel values of the differential image.

Step S206: The image processing unit 421 performs a threshold process. For example, the image processing unit 421 performs the threshold process using a binarization process. The image processing unit 421 generates an image in which one value out of two values is associated with pixels of which pixel values are equal to or larger than a predetermined threshold, and the other value out of the binary values are associated with pixels of which pixel values are equal to or smaller than the predetermined threshold for the pixels of the generated differential image.

In description of the following steps of the image analysis process illustrated in FIG. 7, an image for which the image processes described in in Step S202, Step S204, and Step 206 have been performed will be referred to as a time lapse image TP again.

Step S208: The cell region determining unit 423 determines a cell region in the image P included in the time lapse image TP. Here, the cell region determining unit 423 determines a cell region, for example, using morphology processing. The cell region determining unit 423 determines a cell region by smoothing boundaries for pixels, of which pixel values are equal to or larger than a predetermined threshold, for which the threshold process of Step S207 described above has been performed. In addition, determining of a cell region in an image P will be also referred to as extracting a cell region in the image P.

A technique for determining a cell region using the image processing unit 421 and the cell region determining unit 423 is not limited to that illustrated in the example. The image processing unit 421 and the cell region determining unit 423 may determine a cell region using machine learning, pattern matching, and the like.

The cell region determining unit 423 supplies cell region information representing the determined cell region to the scratch area extracting unit 424 and the calculation unit 426.

Step S210: The scratch area extracting unit 424 performs inversion processing on a cell region in the reference image PS acquired by the cell region determining unit 423. In the inversion processing, the scratch area extracting unit 424 inverts a binarized luminance value of each pixel of the reference image PS.

Here, the reference image PS is automatically selected from the time lapse image TP by the reference image selecting unit 422. For example, the reference image selecting unit 422 selects an image of which a captured time is the earliest in the time lapse image TP. In addition, for example, the reference image selecting unit 422 selects an image P after formation of the scratch area described above from the time lapse image TP or selects an image P that is in a state in which the scratch area described above is formed, and cells have not migrated to the scratched area from the time lapse image TP. The reference image selecting unit 422 supplies reference image information that is information representing the selected reference image PS to the scratch area extracting unit 424. The scratch area extracting unit 424 uses an image P represented by the reference image information supplied from the reference image selecting unit 422 from among images P included in the time lapse image TP as a reference image PS.

Step S212: The scratch area extracting unit 424 sets the result of Step S210 as a scratch area. The scratch area extracting unit 424 extracts an area other than a cell region represented by the cell region information supplied from the cell region determining unit 423 in the entire area included in the reference image PS as a scratch area based on luminance values inverted by performing inversion processing on an image of which the cell region has been extracted. In other words, the scratch area extracting unit 424 recognizes a scratch area by inverting a cell region extracted based on luminance values of the reference image PS.

The scratch area extracting unit 424 supplies scratch area information that is information representing the extracted scratch area to the area setting unit 425.

Step S214: The area setting unit 425 sets a scratch area acquired by the scratch area extracting unit 424 as a reference region RS extracted from the reference image PS. The setting of the reference region RS is setting of an area of pixel values of a scratch area in the reference image PS as a reference region RS in an image (for example, a time lapse image TP) having a cell region and a scratch area as pixels, respectively.

In this embodiment, the reference image PS is an image of which the captured time is the earliest among images P included in the time lapse image TP, and thus the area setting unit 425 sets a scratch area extracted from the image of which the captured time is the earliest from among the images P included in the time lapse image TP as a reference region RS.

The area setting unit 425 supplies the reference region RS and the cell region acquired from the time lapse image TP to the calculation unit 426.

As described above, the area setting unit 425 sets the scratch area formed in the culture area of cells from the reference image PS of the time lapse image TP as a reference region RS. Here, the area setting unit 425 sets the scratch area extracted by the scratch area extracting unit 424 as a reference region RS.

Step S216: The calculation unit 426 determines a cell region included in the reference region RS in a cell region in each image P included in the time lapse image TP. Here, the calculation unit 426 performs determination based on the reference region RS supplied from the area setting unit 425 and the cell region represented by the cell region information supplied from the cell region determining unit 423. The calculation unit 426 determines an area that is common to the reference region RS and the cell region as a cell region included in the reference region RS.

The cell region determined to be included in the reference region RS corresponds to cells infiltrating the scratch area in accordance with migration of cells.

Figure 8:
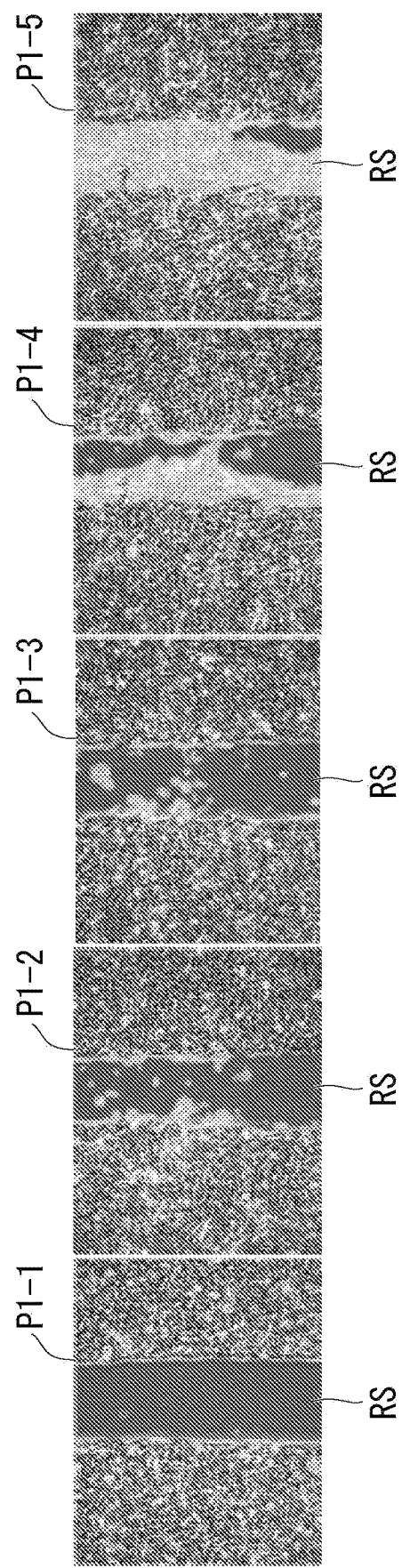
FIG. 8 is a diagram illustrating an example of a scratch area infiltrated by cells according to the first embodiment.

Here, a scratch area (a reference region RS) infiltrated by cells will be described with reference to FIG. 8. FIG. 8 is a diagram illustrating an example of a scratch area infiltrated by cells according to this embodiment. Images P1-1 to P1-5 are images that are extracted from a time lapse image acquired by capturing Mesenchymal stem cells (MSC) for every hour for two days. The images P1-1 to P1-5 are aligned from the left side to the right side in the order of captured times.

The image P1-1 is an image of which a captured time is the earliest and is captured immediately after formation of a scratch area (for example, within several minutes after start of culture or the like), and the scratch area is not infiltrated by cells. In accordance with the elapse of time from the image P1-2 to the image P1-5, cells migrate into the scratch area, and an infiltrated area of the scratch area (in this case, an area of a cell region in the scratch area) increases.

In addition, the calculation unit 426 may determine a cell region that includes a cell region formed as "an outland" in the scratch area and is included in the reference region RS. Here, the cell region formed as "an outland" is a cell region that is included in the scratch area and is an area that is not in contact with a cell region not included in the scratch area. In other words, the cell region formed as "an outland" is a cell region that is included in the scratch area and is an area not connected to a cell region not included in the scratch area. In other words, the calculation unit 426 may determine a cell region included in the reference region RS by including an area that is included in the scratch area and is not connected to a cell region not included in the scratch area.

The description of the image analysis process will be continued with reference back to FIG. 7.

Step S218: The calculation unit 426 calculates an area of cell region within the reference region RS from each of the time lapse image TP. Here, by measuring the number of pixels of the cell region included in the reference region RS determined in Step S216, the calculation unit 426 calculates the area of the cell region within the reference region RS. The calculation unit 426 supplies the calculated area of the cell region within the reference region RS to the display control unit 427.

Here, as described above, the cell region within the reference region RS is determined by the calculation unit 426 as an area that is commonly included in the reference region RS and the cell region represented by the cell region information in the reference region RS. In other words, a cell region within the reference region RS is determined based on the cell region that has been determined in advance in the image P. Thus, the calculation unit 426 calculates an area of the cell region within the reference region RS based on the cell region in the image P included in the time lapse image TP.

Step S220: The display control unit 427 outputs a change in the time series of the area of the cell region within the reference region RS that is calculated by the calculation unit 426 to the display unit 44 as analysis information and causes the display unit to display the change.

As above, the arithmetic operation unit 42 ends the image analysis process.

Figure 9:
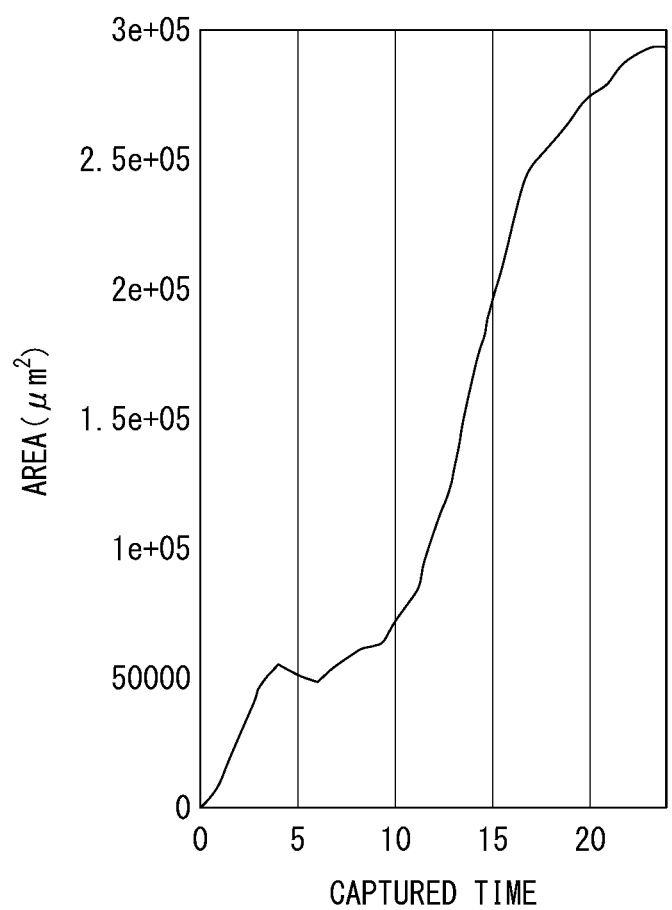
FIG. 9 is a diagram illustrating an example of a change in a time series of an area of a cell region within a reference region according to the first embodiment.

Here, a change in the time series of the area of a cell region within the reference region RS will be described with reference to FIG. 9. FIG. 9 is a diagram illustrating an example of a change in a time series of an area of a cell region within a reference region RS according to this embodiment. In a graph illustrated in FIG. 9, in an image P included in a time lapse image TP, the area of the cell region within the reference region RS is plotted with respect to the captured time. From the graph illustrated in FIG. 9, it can be understood that the area of the cell region within the reference region RS tends to increase in accordance with elapse of the captured time. For example, the change in the time series of the area of the cell region within the reference region RS is used for a quantitative evaluation of the migration ability of cells.

In addition, in addition to the change in the time series of the area of the cell region within the reference region RS, as illustrated in FIG. 8 described above, the display control unit 427 may set a predetermined color to pixels corresponding to the cell region within the reference region RS in the image P and cause the display unit 44 to display the image P included in the time lapse image TP. Here, for example, it is preferable that the predetermined color be a color that can be easily visually identified from pixels to which the predetermined color is not set, such as green, yellow green, or the like. In a case in which the display control unit 427 causes the display unit 44 to display the image P with a predetermined color set to pixels corresponding to the cell region, the calculation unit 426 supplies information representing a time lapse image TP and a cell region within the reference region RS in the image P included in the time lapse image TP to the display control unit 427.

In addition, in this embodiment, although an example of a case in which a cell region within the reference region RS is determined as an area that is commonly included in the reference region RS and the cell region represented by the cell region information, in other words, an example of a case in which a cell region within the reference region RS is determined based on the cell region determined in advance in the image P has been described, the configuration is not limited thereto. A cell region may be directly determined within the reference region RS without determining a cell region in the image P in advance.

In a case in which a cell region is directly determined within the reference region RS, for example, the cell region determining unit 423 determines a cell region within the reference region RS. In other words, the cell region determining unit may determine a cell region based on the scratch area extracted by the scratch area extracting unit 424.

In addition, in this embodiment although an example of a case in which the area of a cell region within the reference region RS is calculated based on the cell region has been described, the configuration is not limited thereto. The area of the cell region within the reference region RS may be calculated based on the scratch area.

In a case in which the area of the cell region within the reference region RS is calculated based on the scratch area, for example, the scratch area extracting unit 424 extracts a scratch area for each image P included in the time lapse image TP. Here, the scratch area, for example, is extracted through image recognition using machine learning. The calculation unit 426 calculates an area of a cell region within the reference region RS for an image P captured at a certain captured time based on a difference between the area of a scratch area extracted from an image P captured at the certain captured time and the area of a scratch area extracted from the reference image PS.

In addition, in this embodiment, although an example of a case in which the scratch area extracting unit 424 extracts a scratch area from the reference image PS, and the area setting unit 425 sets the scratch area extracted by the scratch area extracting unit 424 as a reference region RS has been described, the configuration is not limited thereto. A scratch area may be designated by an observer.

In a case in which a scratch area is designated by an observer, the arithmetic operation unit 42, for example, includes an operation information acquiring unit. This operation information acquiring unit acquires operation information representing a scratch area designated by the observer in the reference image PS. Here, the observer designates a scratch area through the operation unit 45. The observer, for example, designates a scratch area by drawing lines using a mouse, a touch pen, or the like in the reference image PS displayed on the display unit 44. The observer may designate a scratch area by input a plurality of coordinates for designating a shape such as a polygon from the operation unit 45 in the reference image PS displayed in the display unit 44. The area setting unit 425 sets the scratch area represented by the operation information accepted by the operation information acquiring unit as a reference region RS.

In addition, in this embodiment, although an example of a case in which an image of which a captured time is the earliest is selected from the time lapse image TP as a reference image PS has been described, the configuration is not limited thereto. As the reference image PS, an image other than the image of which the captured time is the earliest may be selected as long as the image is an image captured in a time period in which cells have not migrated to a scratch area after the scratch area is formed. For example, in a case in which cells have not migrated to a scratch area, the reference image selecting unit 422 may select an image of which the captured time is the second earliest, the third earliest, or the like as the reference image PS.

As described above, the image analyzer (a device including the arithmetic operation unit 42 according to this embodiment) according to this embodiment includes the area setting unit 425 and the calculation unit 426. The area setting unit 425 sets a scratch area formed in the culture area of cells from the reference image PS of the time lapse image TP as a reference region RS. The calculation unit 426 calculates an area of each cell region of cells within the reference region RS from the time lapse image TP.

By employing this configuration, the image analyzer according to this embodiment can calculate a change (for example, an increase/decrease) in the time series of the area of the cell region in the scratch area infiltrated by the cells and thus can quantitatively evaluate migration ability of the cells.

In addition, the image analyzer according to this embodiment includes a control unit (the display control unit 427 according to this embodiment). The control unit (the display control unit 427 according to this embodiment) causes a display device (the display unit 44 according to this embodiment) to display a change in the time series of the area of the cell region of cells within the reference region RS calculated by the calculation unit 426.

By employing this configuration, the image analyzer according to this embodiment can display a change in the time series of the area of the cell region within the scratch area and thus can visualize the migration ability of the cells.

In addition, in the image analyzer according to this embodiment, the calculation unit 426 calculates the area of a cell region occupied within the reference region RS based on the cell region in an image P included in the time lapse image TP.

By employing this configuration, the image analyzer according to this embodiment can calculate the area of a cell region in the scratch area based on the cell region and thus can quantitatively evaluate the migration ability of cells using a simpler analysis than that of a case in which the area of a cell region in the scratch area is calculated based on the scratch area. In a case in which the area of a cell region in the scratch area is calculated based on a clutch area, for example, the scratch area is determined based on machine learning. As described above, in the image analyzer according to this embodiment, a cell region is determined through edge detection, and thus the analysis is simpler than in a case in which a scratch area is extracted using machine learning.

In addition, the image analyzer according to this embodiment includes the cell region determining unit 423. The cell region determining unit 423 determines a cell region of cells in an image P included in the time lapse image TP.

By employing this configuration, the image analyzer according to this embodiment can determine a cell region of cells in an image P included in the time lapse image TP and thus can perform various analyses of cells in addition to an analysis quantitatively evaluating the migration ability of the cells. Here, various analyses of cells, for example, include tracking of the cells, an analysis of a degree of maturity of cells based on a density of the cells, an analysis based on feature quantities extracted from an image of the cells, and the like.

In addition, the image analyzer according to this embodiment includes the scratch area extracting unit 424. The scratch area extracting unit 424 extracts a scratch area from the reference image PS based on a luminance value of the reference image PS. The area setting unit 425 sets the scratch area extracted by the scratch area extracting unit 424 as a reference region RS.

By employing this configuration, in the image analyzer according to this embodiment, a scratch area extracted from the reference image is set as a reference region RS, and thus a user's effort for designating a reference region can be saved.

In addition, the image analyzer according to this embodiment may include the operation information acquiring unit. This operation information acquiring unit acquires operation information representing a scratch area designated by a user (an observer according to this embodiment) in the reference image PS. The area setting unit 425 sets the scratch area represented by the operation information accepted by the operation information acquiring unit as a reference region RS.

By employing this configuration, in the image analyzer according to this embodiment, a user can set a reference region, and thus even in a case in which accuracy of extraction of a scratch area in the image analysis process of an image P included in the time lapse image TP is not sufficiently high, the user can quantitatively evaluate the migration ability of cells based on the reference region set by the user.

In addition, the image analyzer according to this embodiment includes the reference image selecting unit 422. The reference image selecting unit 422 selects a reference image PS from the time lapse image TP.

By employing this configuration, the image analyzer according to this embodiment can select a reference image PS from the time lapse image TP, and thus, a user's effort for selecting the reference image PS can be saved.

In addition, the cell culture observation device according to this embodiment (the incubator 11 according to this embodiment) includes the image analyzer described above, a culture device (the thermostatic chamber 15 according to this embodiment), and a microscope (the observation unit 22 according to this embodiment). The culture device (the thermostatic chamber 15 according to this embodiment) cultures cells housed in the culture container. The microscope (the observation unit 22 according to this embodiment) captures a time lapse image TP.

By employing this configuration, the cell culture observation device according to this embodiment (the incubator 11 according to this embodiment) can calculate a change in the time series of the area of the scratch area infiltrated by cells and thus can quantitatively evaluate the migration ability of the cells.

Second Embodiment

Hereinafter, a second embodiment will be described in detail with reference to the drawings.

In the first embodiment described above, a case in which the image analyzer calculates the area of a cell region in the scratch area in the time lapse image has been described. In this embodiment, a case in which an image analyzer calculates a ratio of the area of a cell region to a scratch area in a time lapse image will be described. Hereinafter, a ratio of the area of a cell region to the scratch area will be also referred to as a scratch area closure ratio.

An arithmetic operation unit according to this embodiment will be referred to as an arithmetic operation unit 42a. An image analyzer according to this embodiment is a device that includes the arithmetic operation unit 42a.

Figure 10:
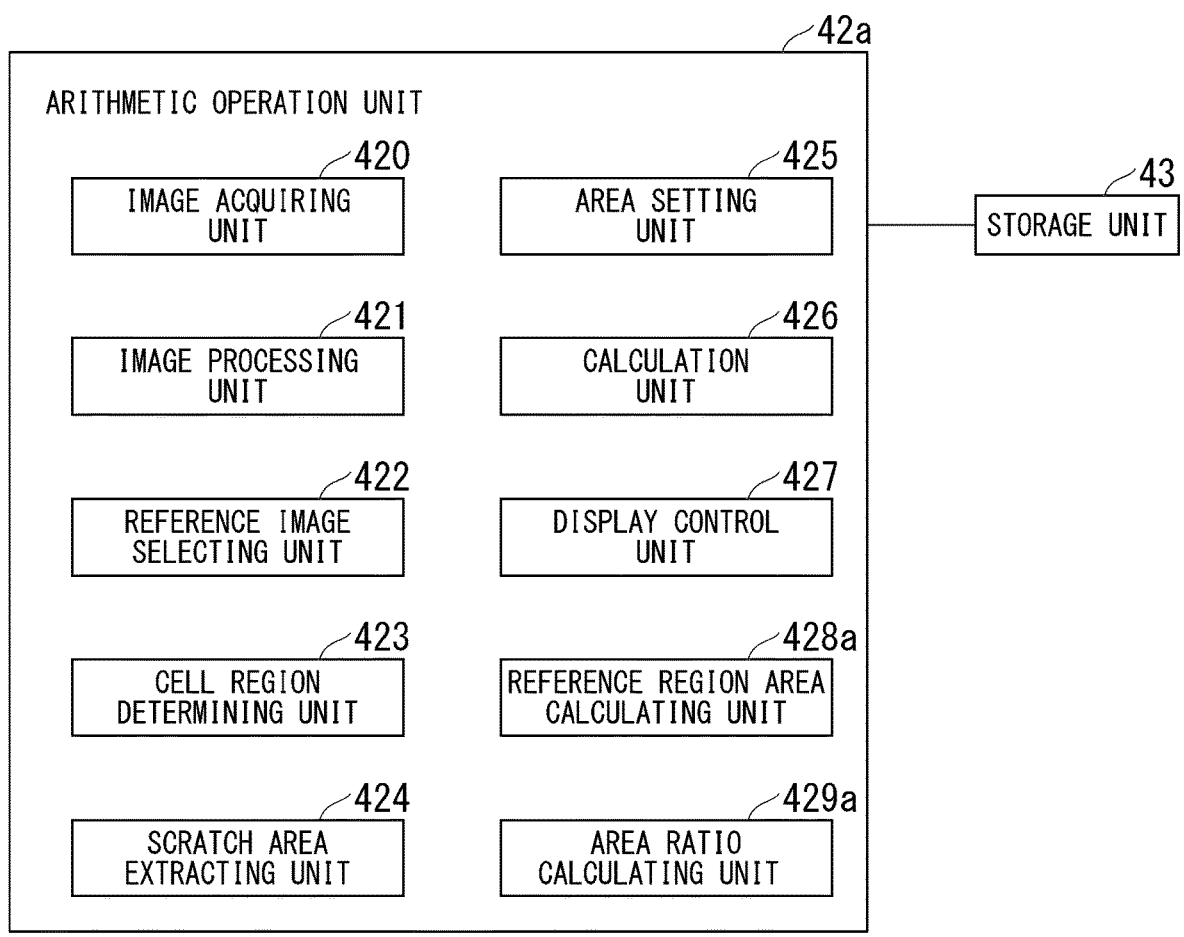
FIG. 10 is a diagram illustrating an example of the functional configuration of an arithmetic operation unit according to a second embodiment.

FIG. 10 is a diagram illustrating an example of the functional configuration of the arithmetic operation unit 42a according to this embodiment. The arithmetic operation unit 42a includes an image acquiring unit 420, an image processing unit 421, a reference image selecting unit 422, a cell region determining unit 423, a scratch area extracting unit 424, an area setting unit 425, a calculation unit 426, a display control unit 427, a reference region area calculating unit 428a, and an area ratio calculating unit 429a.

When the arithmetic operation unit 42a (FIG. 10) according to this embodiment is compared with the arithmetic operation unit 42 (FIG. 6) according to the first embodiment, the reference region area calculating unit 428a and the area ratio calculating unit 429a are different. Here, the functions of the other constituent elements (the image acquiring unit 420, the image processing unit 421, the reference image selecting unit 422, the cell region determining unit 423, the scratch area extracting unit 424, the area setting unit 425, the calculation unit 426, and the display control unit 427) are the same as those according to the first embodiment. Description of the functions that are the same as those according to the first embodiment will be omitted, and in the second embodiment, parts different from the first embodiment will be described.

The reference region area calculating unit 428a calculates an area of a reference region RS.

The area ratio calculating unit 429a calculates a ratio of the area of a cell region occupied within a reference region RS to the area of the reference region RS based on the area of the reference region RS and the area of the cell region in the reference region RS. In other words, the area ratio calculating unit 429a calculates a scratch area closure ratio.

Figure 11:
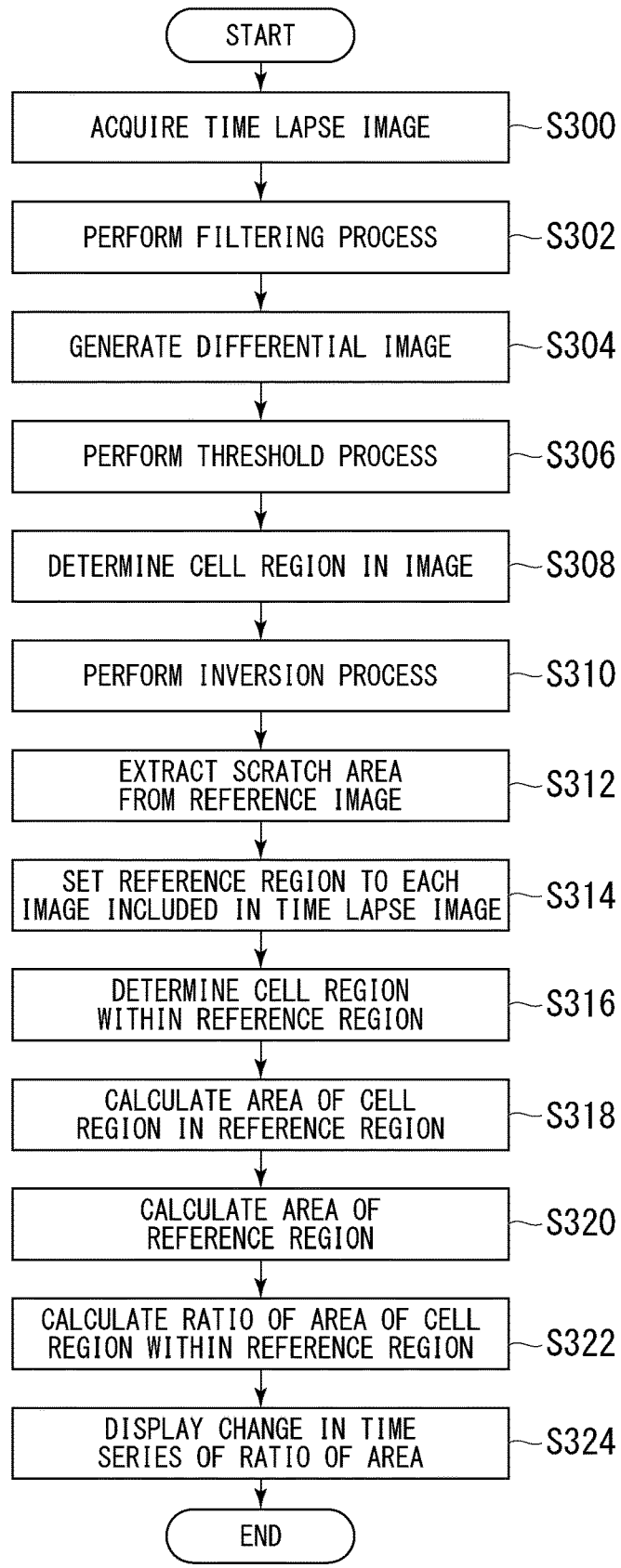
FIG. 11 is a diagram illustrating an example of an image analysis process according to the second embodiment.

Next, an image analysis process of the arithmetic operation unit 42a will be described with reference to FIG. 11. FIG. 11 is a diagram illustrating an example of the image analysis process according to this embodiment.

In addition, each of the processes of Steps S300, S302, S304, S306, S308, S310, S312, S314, S316, and S318 are similar to each of the processes of Steps S200, S202, S204, S206, S208, S210, S212, S214, S216, and S218 illustrated in FIG. 7, and thus description thereof will be omitted.

Step S320: The reference region area calculating unit 428a calculates the area of a reference region RS based on a reference image PS. The reference image PS, for example, is an image P of which a captured time is the earliest in a time lapse image TP, and thus, in other words, the reference region area calculating unit 428a calculates an area of a scratch area in the image P of which the captured time is the earliest in the time lapse image TP.

Here, by measuring the number of pixels of the reference region RS in the reference image PS, the reference region area calculating unit 428a calculates an area of the reference region RS. The reference region area calculating unit 428a, for example, calculates the area of a scratch area in the reference image PS based on the scratch area extracted by the scratch area extracting unit 424. In addition, the reference region area calculating unit 428a may calculate an area of the reference region RS using an area other than a determine cell region as a scratch area based on the cell region determined by the cell region determining unit 423.

The reference region area calculating unit 428a supplies the calculated area of the reference region RS to the area ratio calculating unit 429a.

Figure 12:
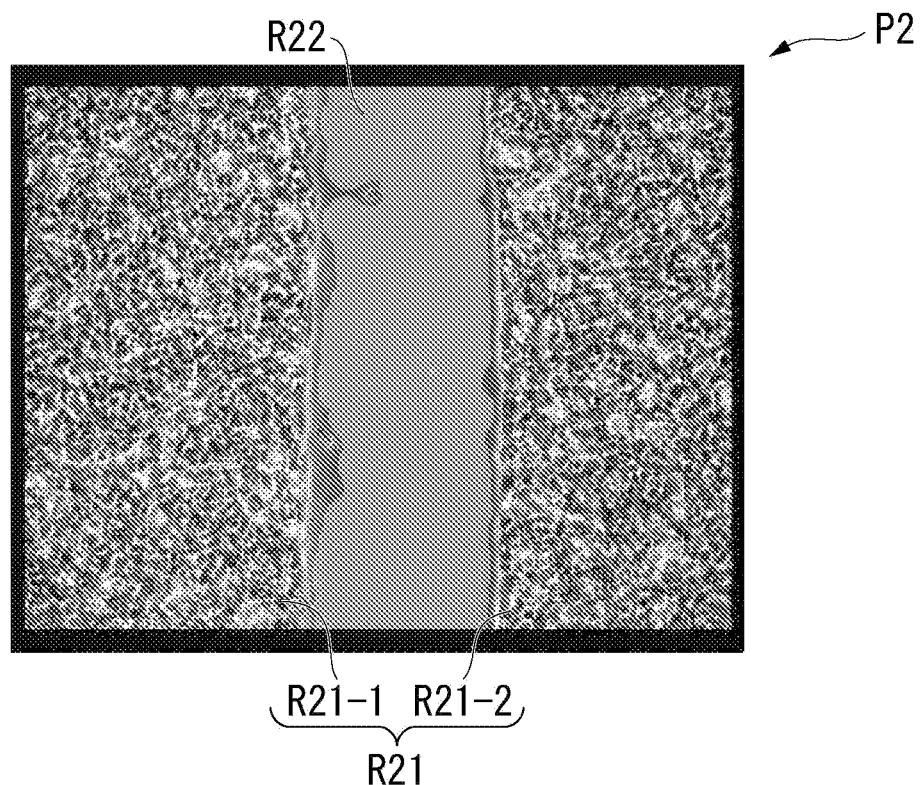
FIG. 12 is a diagram illustrating an example of the area of a scratch area according to the second embodiment.

Here, the area of a scratch area will be described with reference to FIG. 12. FIG. 12 is a diagram illustrating an example of the area of a scratch area according to this embodiment. In FIG. 12, an image P2 is illustrated as an example of the image P included in the time lapse image TP. The image P2 is an image captured after elapse of a predetermined time from formation of a scratch area.

In the image P2, a culture area R21 is illustrated as a culture area of cells. The culture area R21 is formed from a culture area R21-1 and a culture area R21-2, and a scratch area R22 is formed between the culture area R21-1 and the culture area R21-2. As illustrated in FIG. 12, the shape of the scratch area R22 is deformed from the form of a belt shape due to the scratch area infiltrated by cells disposed in left and right cell regions.

The description of the image analysis process will be continued with reference back to FIG. 11.

Step S322: The area ratio calculating unit 429a calculates a ratio of the area of the cell region occupied within the reference region RS to the reference region RS based on the area of the reference region RS calculated by the reference region area calculating unit 428a and the area of the cell region in the reference region RS that is calculated by the calculation unit 426. Here, the area ratio calculating unit 429a calculates a ratio of the area of a cell region occupied within the reference region RS to the reference region RS for each image P included in a time lapse image TP. In addition, the area of the cell region is supplied from the calculation unit 426 to the area ratio calculating unit 429a for each image P included in the time lapse image TP.

The area ratio calculating unit 429a supplies the calculated area ratio to the display control unit 427 as analysis information.

Step S324: The display control unit 427 outputs a change in the time series of the ratio of the area of the cell region occupied within the reference region RS to the reference region RS that is calculated by the area ratio calculating unit 429a to the display unit 44 as analysis information and causes the display unit to display the change.

As above, the arithmetic operation unit 42 ends the image analysis process.

Figure 13:
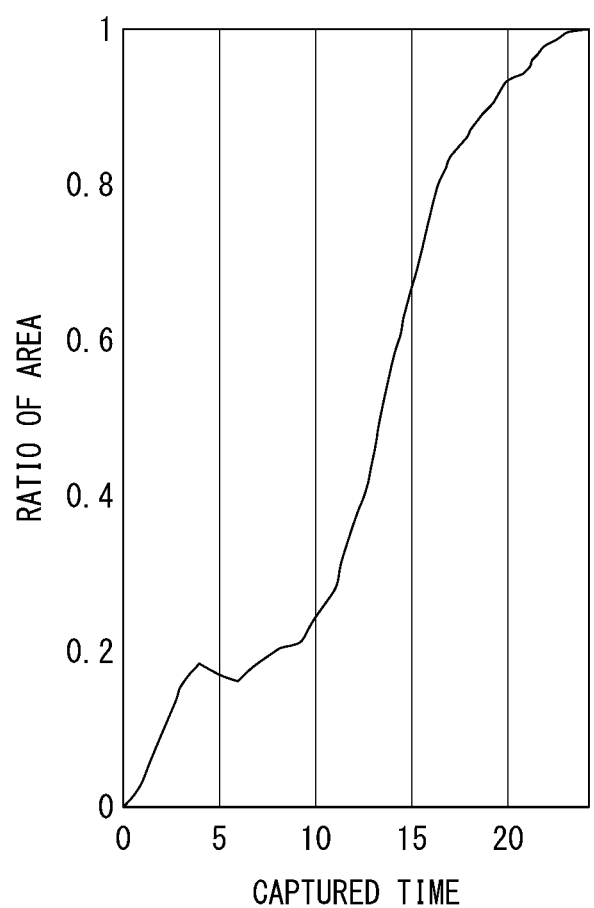
FIG. 13 is a diagram illustrating an example of a change in a time series of the ratio of an area of a cell region within a reference region to the reference region according to the second embodiment.

Here, a change in the time series of the ratio of the area of the cell region within the reference region RS to the reference region RS will be described with reference to FIG. 13. FIG. 13 is a diagram illustrating an example of a change in a time series of a ratio of an area of a cell region within a reference region RS to the reference region RS according to this embodiment. In a graph illustrated in FIG. 13, a ratio of the area of a cell region within a reference region RS to the reference region RS is plotted with respect to the captured time for an image P included in the time lapse image TP. From the graph illustrated in FIG. 13, it can be understood that the ratio of the area of the cell region within the reference region RS to the reference region RS tends to increase in accordance with elapse of the captured time. For example, the change in the time series of the ratio of the area of the cell region within the reference region RS to the reference region RS is used for a quantitative evaluation of the migration ability of cells.

As described above, an image analyzer according to this embodiment (a device including the arithmetic operation unit 42a according to this embodiment) includes the reference region area calculating unit 428a and the area ratio calculating unit 429a. The reference region area calculating unit 428a calculates an area of a reference region RS. The area ratio calculating unit 429a calculates the ratio of the area of a cell region occupied within a reference region RS to the reference region RS based on the area of the reference region RS calculated by the reference region area calculating unit 428a and the area of the cell region calculated by the calculation unit 426.

By employing this configuration, the image analyzer according to this embodiment can calculate a scratch area closure rate and thus can quantitatively evaluate the migration ability of cells based on the scratch area closure rate.

Third Embodiment

Hereinafter, a third embodiment will be described in detail with reference to the drawings.

In the first embodiment and the second embodiment, a case in which the image analyzer calculates an area of a cell region in a scratch area in the time lapse image and a ratio of the area has been described. In this embodiment, a case in which an image analyzer evaluates the migration ability of cells based on an area or the ratio of an area of a cell region in a scratch area to the scratch area will be described.

An arithmetic operation unit according to this embodiment will be referred to as an arithmetic operation unit 42b. An image analyzer according to this embodiment is a device that includes the arithmetic operation unit 42b.

Figure 14:
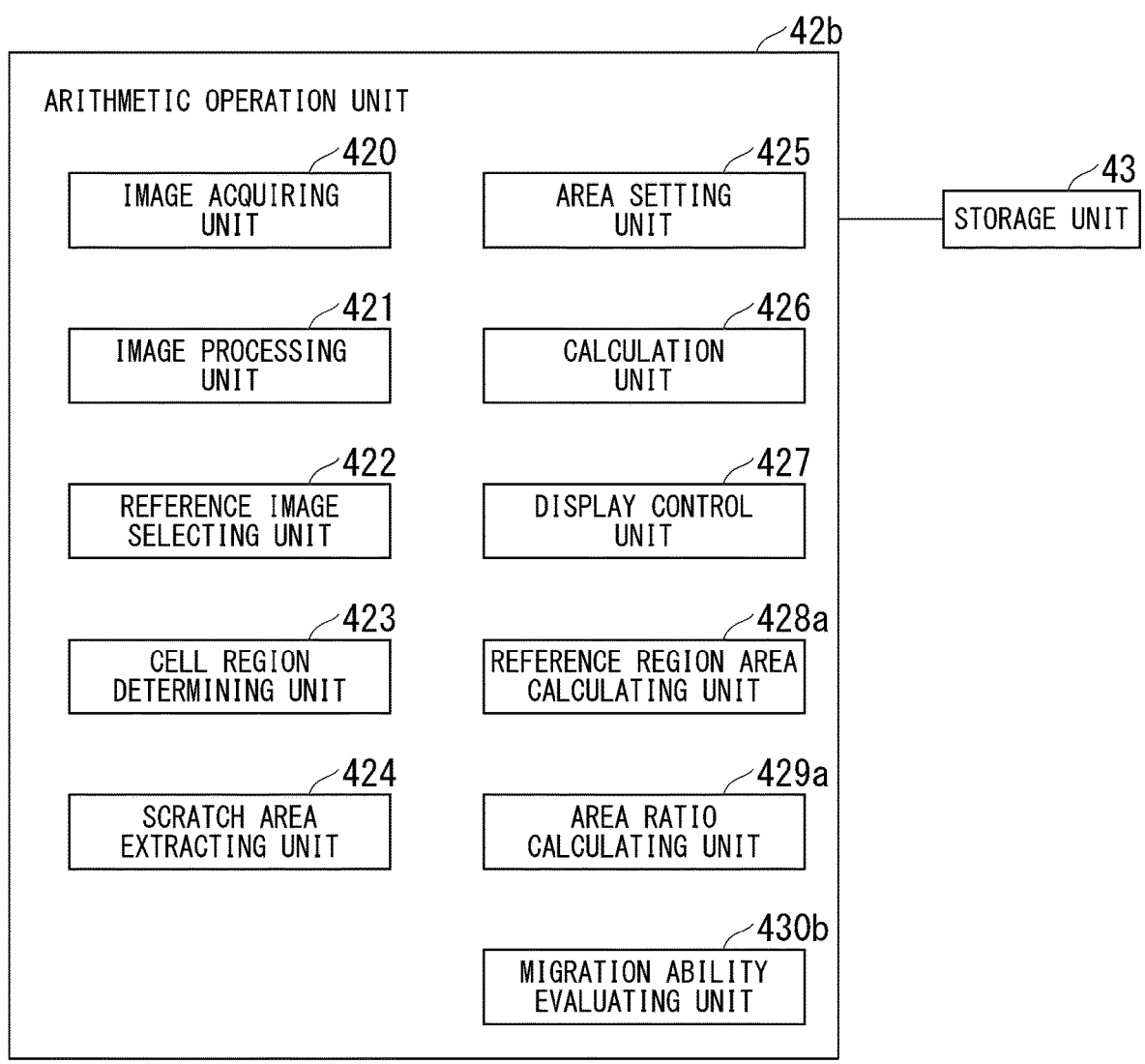
FIG. 14 is a diagram illustrating an example of the functional configuration of an arithmetic operation unit according to a third embodiment.

FIG. 14 is a diagram illustrating an example of the functional configuration of the arithmetic operation unit 42b according to this embodiment. The arithmetic operation unit 42b includes an image acquiring unit 420, an image processing unit 421, a reference image selecting unit 422, a cell region determining unit 423, a scratch area extracting unit 424, an area setting unit 425, a calculation unit 426, a display control unit 427, a reference region area calculating unit 428a, an area ratio calculating unit 429a, and a migration ability evaluating unit 430b.

When the arithmetic operation unit 42b (FIG. 14) according to this embodiment is compared with the arithmetic operation unit 42a (FIG. 10) according to the second embodiment, the migration ability evaluating unit 430b is different. Here, the functions of the other constituent elements (the image acquiring unit 420, the image processing unit 421, the reference image selecting unit 422, the cell region determining unit 423, the scratch area extracting unit 424, the area setting unit 425, the calculation unit 426, the display control unit 427, the reference region area calculating unit 428a, and the area ratio calculating unit 429a) are the same as those according to the first embodiment and the second embodiment. Description of the functions that are the same as those according to the first embodiment and the second embodiment will be omitted, and in the third embodiment, parts different from the first embodiment and the second embodiment will be described.

The migration ability evaluating unit 430b evaluates the migration ability of cells based on a change in a time series of an area of a cell region in a reference region RS and/or a change in the time series of the ratio of the area.

Figure 15:
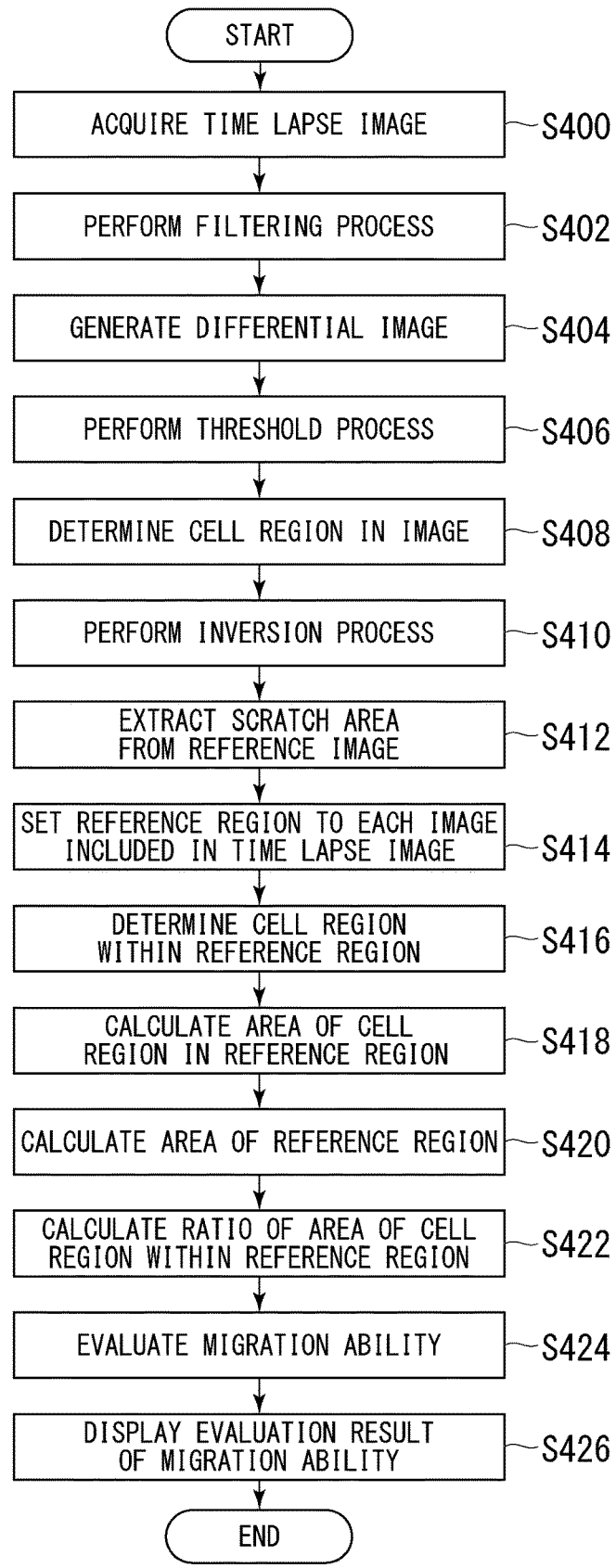
FIG. 15 is a diagram illustrating an example of a migration ability evaluating process according to the third embodiment.

Next, a migration ability evaluating process of the arithmetic operation unit 42b will be described with reference to FIG. 15. FIG. 15 is a diagram illustrating an example of the migration ability evaluating process according to this embodiment.

In addition, processes of Steps S400, S402, S404, S406, S408, S410, S412, S414, S416, S418, S420, and S422 are similar to the processes of Steps S300, S302, S304, S306, S308, S310, S312, S314, S316, S318, S320, and S322 illustrated in FIG. 11, and thus description thereof will be omitted.

Step S424: The migration ability evaluating unit 430b evaluates the migration ability of cells based on a change in the time series of an area of a cell region in a reference region RS that is calculated by the calculation unit 426 and/or a change in a time series of a ratio of an area calculated by the area ratio calculating unit 429a. The migration ability evaluating unit 430b supplies an evaluation result of the migration ability to the display control unit 427 as analysis information.

For example, the migration ability evaluating unit 430b determines migration ability based on whether an area of a cell region in a reference region RS is equal to or larger than a predetermined threshold until elapse of a predetermined time after start of capturing of a time lapse image TP based on a change in a time series of the area of the cell region in the reference region RS. In a case in which it is determined that the area of the cell region in the reference region RS is equal to or larger than the predetermined threshold until a predetermined time, the migration ability evaluating unit 430b determines that the migration ability is high. On the other hand, in a case in which it is determined that the area of the cell region in the reference region RS is smaller than the predetermined threshold until a predetermined time, it is determined that the migration ability is low.

The migration ability evaluating unit 430b may determine the migration ability based on whether a ratio of an area of a cell region in a reference region RS to the reference region RS is equal to or larger than a predetermined threshold until elapse of a predetermined time after start of capturing of a time lapse image TP based on a change in a time series of the ratio of the area of the cell region in the reference region RS reference region RS. In a case in which it is determined that the ratio of the area of the cell region in the reference region RS is equal to or larger than the predetermined threshold until elapse of the predetermined time, the migration ability evaluating unit 430b determines that the migration ability is high. On the other hand, in a case in which it is determined that the ratio of the area of the cell region in the reference region RS is smaller than the predetermined threshold until elapse of the predetermined time, it is determined that the migration ability is low.

In addition, the migration ability evaluating unit 430b may evaluate migration abilities of cells of different kinds by comparing changes in time series of areas of cell regions in reference regions RS and/or ratios of the areas between cells of the different kinds based on time lapse images TP captured through time lapse imaging of the cells of the different kinds that have been cultured under the same conditions. Here, the cells of different kinds, for example, are cultured respectively in different wells on a well plate that is a culture container. For example, the same conditions are conditions of the widths of the belt-shaped scratch areas formed in the culture area being the same.

For example, the migration ability evaluating unit 430b determines cells exhibiting a scratch area closure rate of a predetermined ratio or more after elapse of a predetermined time to have a high migration ability. Here, for example, the predetermined time is 24 hours.

Here, the kinds of cells, for example, are kinds according to differences in the origination or kinds according to differences in passage numbers.

As the kinds of cells according to differences in the origination, for example, there are MSC originated from fat and MSC originated from the bone marrow. In addition, as the kinds of cells according to differences in the origination, for example, there are kinds according to lot differences using donors. As the culture state of cells is better, the migration ability becomes higher, and thus a speed at which the scratch area is infiltrated becomes higher. In other words, it is assumed that the culture state becomes better as a change in the time series of the scratch area closure ratio is larger.

As kinds of cells according to differences in the differences in passage numbers, there are young cells of which a passage number is small and old cells of which a passage number is large. A young cell has a higher migration ability than an old cell, and thus a speed at which the scratch area is infiltrated becomes higher. In other words, as the ratio of an increase in the time series of the scratch area closure ratio is higher, a younger cell of which the passage number is smaller is assumed.

The migration ability evaluating unit 430b may determine whether or not the culture state is good, whether or not the cell is a young cell, and the like based on an evaluation result of the migration ability and supply the evaluation result of the migration ability to the display control unit 427 with such a determination result included therein.

Step S426: The display control unit 427 outputs the evaluation result of the migration ability evaluated by the migration ability evaluating unit 430b to the display unit 44 as analysis information and causes the display unit to display the evaluation result. Here, the display control unit 427, for example, causes the display unit 44 to display the evaluation result of the migration ability as a text. In a case in which the evaluation result indicates a high migration ability, this text, for example, is "Migration ability: High" or the like.

As above, the arithmetic operation unit 42 ends the migration ability evaluating process.

As described above, an image analyzer according to this embodiment (a device including the arithmetic operation unit 42b) includes an evaluation unit (the migration ability evaluating unit 430b in this embodiment). The evaluation unit (the migration ability evaluating unit 430b in this embodiment) evaluates the migration ability of cells based on a change in the time series of the area of the cell region that is calculated by the calculation unit 426.

By employing this configuration, the image analyzer according to this embodiment can evaluate the migration ability of cells based on the change in the time series of the area of a cell region in a scratch area, and thus quantitative evaluation of the migration ability of cells can be performed.

Fourth Embodiment

Hereinafter, a fourth embodiment will be described in detail with reference to the drawings.

In this embodiment, a case in which an image analyzer visualizes the migration ability of cells using a graphical user interface (GUI) based on an area of a cell region in the scratch area or a ratio of the area of a cell region in the scratch area to the scratch area described above will be described.

An arithmetic operation unit according to this embodiment will be referred to as an arithmetic operation unit 42c. An image analyzer according to this embodiment is a device that includes the arithmetic operation unit 42c. In addition, the arithmetic operation unit 42c has a function of a display control unit 427 that is different from the arithmetic operation unit 42 (FIG. 6) according to the first embodiment, the arithmetic operation unit 42a (FIG. 10) according to the second embodiment, and the arithmetic operation unit 42b (FIG. 14) according to the third embodiment. Here, the functions of the other constituent elements (an image acquiring unit 420, an image processing unit 421, a reference image selecting unit 422, a cell region determining unit 423, a scratch area extracting unit 424, an area setting unit 425, a calculation unit 426, a display control unit 427, a reference region area calculating unit 428a, an area ratio calculating unit 429a, and a migration ability evaluating unit 430b) are the same as those according to the first embodiment, the second embodiment, and the third embodiment. Description of the functional configuration of the arithmetic operation unit 42c will be omitted, and, in the fourth embodiment, a screen of a GUI that a display control unit 427 causes a display unit 44 to display will be described.

Hereinafter, a screen D1, a screen D2, and a screen D3 of the GUI that the display control unit 427 causes the display unit 44 to display will be described with reference to FIGS. 16 to 18. In addition, the screen D1, the screen D2, and the screen D3 of the GUI are displayed in the display unit 44 using a dedicated application or are displayed in the display unit 44 using a web browser.

Figure 16:
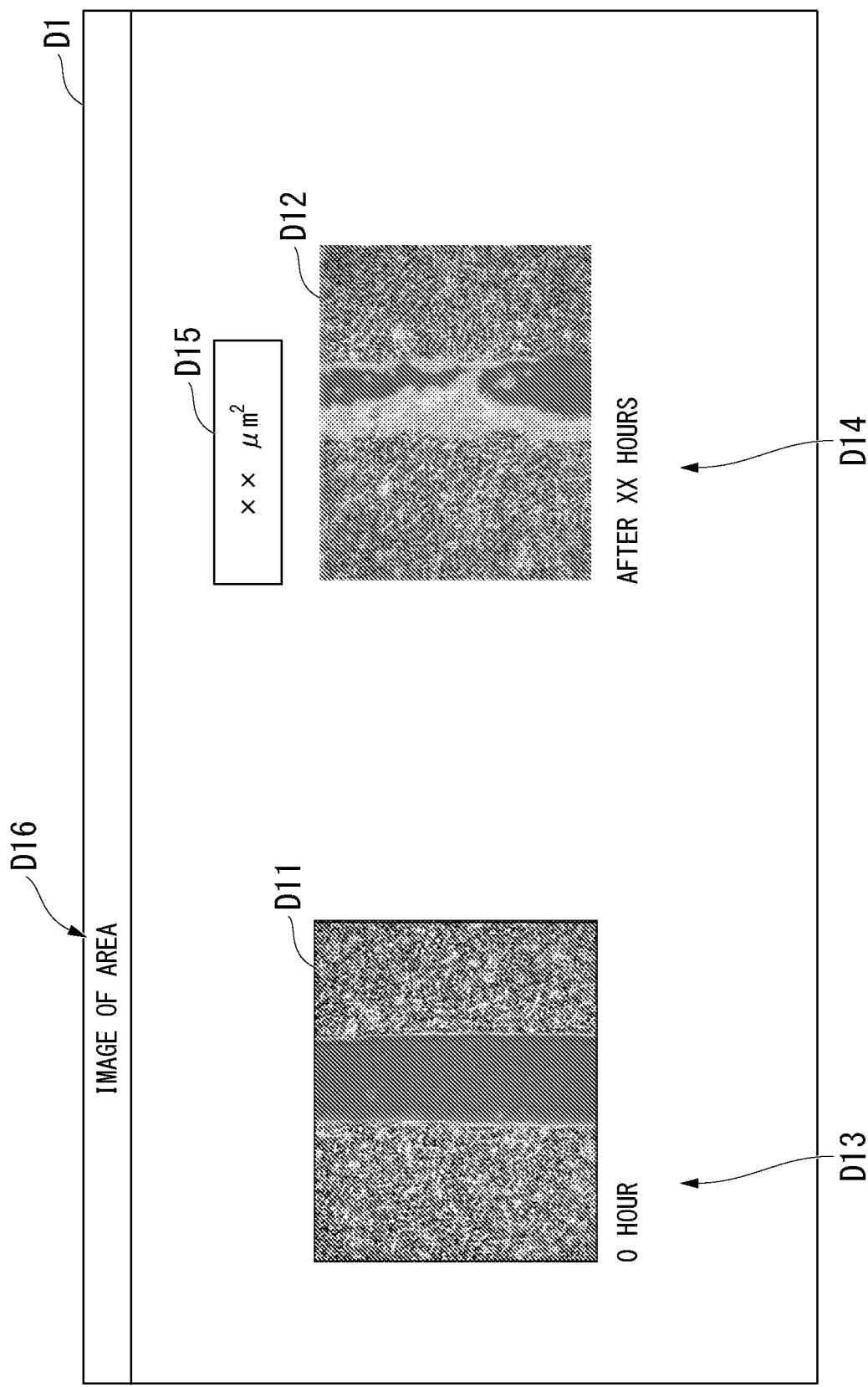
FIG. 16 is a diagram illustrating an example of a screen of a GUI according to a fourth embodiment.

FIG. 16 is a diagram illustrating an example of the screen D1 of the GUI according to this embodiment. The display control unit 427 displays the screen D1 based on an area of a cell region in a reference region RS. The screen D1 is configured to include a screen D11, a screen D12, a text D13, a text D14, a display window D15, and a text D16 as a plurality of display fields.

A reference image PS is displayed on the screen D11. As described above, the reference image PS is an image of which a captured time is the earliest among images P included in the time lapse image TP, and the scratch area is not infiltrated by cells. The text D13 represents time information of an elapsed time or a captured time of the reference image PS displayed on the screen D11.

On the screen D12, for example, an image captured at a latest captured time among images P included in the time lapse image TP is displayed. In other words, the display control unit 427 immediately displays an image captured through time lapse capturing on the screen D12.

Here, the display control unit 427 displays the image P by illustrating a cell region in the reference region RS of the image P. For example, the display control unit 427 illustrates a cell region by setting a predetermined color to pixels corresponding to a cell region in the reference region RS of the image P. Each time time lapse capturing is performed and a new image P is captured, the display control unit 427 updates the image P displayed on the screen D12.

The text D14 represents time information of an elapsed time or a captured time of the image P displayed on the screen D12. The display window D15 represents a value of an area of the cell region in the reference region RS of the image P displayed on the screen D12.

The text D16 represents a title of the screen D1. In the example illustrated in FIG. 16, the screen D1 is displayed based on the area of the cell region in the reference region RS, and thus the text D16 is displayed as "Image of Area".

In addition, the display control unit 427 may display the screen D1 based on a ratio of the area of the cell region in the reference region RS to the reference region RS. In such a case, the display control unit 427 displays the image P by illustrating an area other than the cell region in the reference region RS of the image P. For example, the display control unit 427 performs display by setting a predetermined color to pixels corresponding to an area other than the cell region in the reference region RS of the image P. In this case, the display window D15 represents a ratio of the area of the cell region in the reference region RS to the reference region RS of the image P displayed on the screen D12 (in other words, a scratch area closure ratio).

In addition, the display control unit 427 may display the screen D1 based on both the area of the cell region in the reference region RS and the ratio of the area of the cell region in the reference region RS to the reference region RS. In such a case, the display control unit 427 performs display by aligning both an image in which the cell region in the reference region RS of the image P is illustrated and an image in which an area other than the cell region in the reference region RS of the image P is illustrated on the screen D12.

A kind of image displayed on the screen D12 by the display control unit 427 may be selected by a user from the image in which the cell region in the reference region RS of the image P is illustrated and the image in which an area other than the cell region in the reference region RS of the image P is illustrated.

Figure 17:
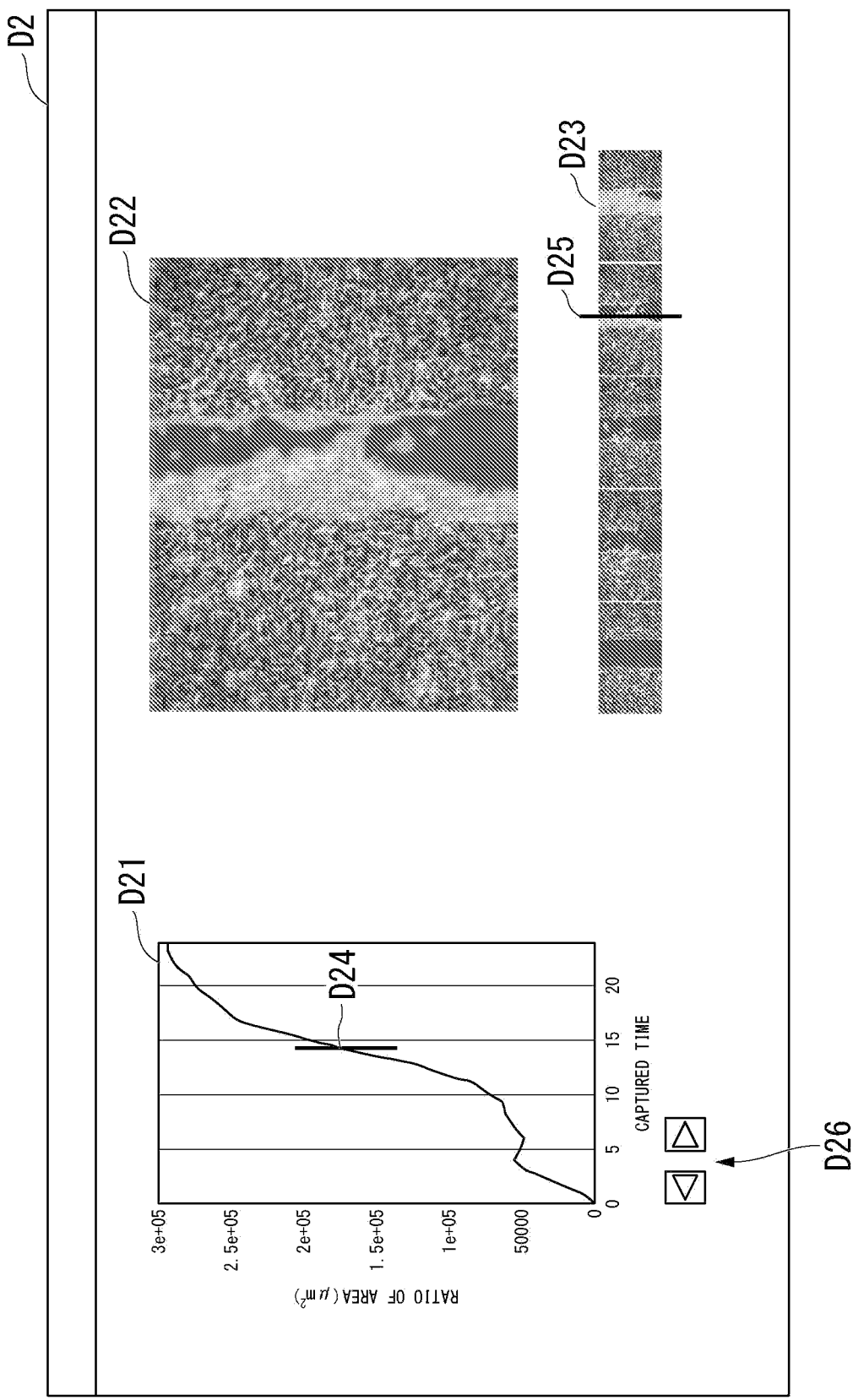
FIG. 17 is a diagram illustrating an example of a screen of a GUI according to the fourth embodiment.

FIG. 17 is a diagram illustrating an example of the screen D2 of the GUI according to this embodiment. The display control unit 427 displays the screen D2 based on the area of the cell region in the reference region RS. The screen D2 is configured to include a screen D21, a screen D22, a screen D23, a bar D24, a bar D25, and a button D26 as a plurality of display fields.

On the screen D21, a graph representing a change in the time series of the area of the cell region within the reference region RS is displayed. The graph displayed on this screen D21, for example, is the graph as illustrated in FIG. 9.

On the screen D22, a time lapse image TP is displayed as a moving image. Here, the image P included in the time lapse image TP is displayed as an image in which the cell region is illustrated in the reference region RS. The display control unit 427 selects an image displayed on the screen D22 among images P included in the time lapse image TP based on a time parameter. The time parameter is associated with a captured time of the time lapse image TP. When reproduction of the moving image starts, the value of the time parameter increases over time in accordance with a reproduction speed.

Here, in the graph displayed on the screen D21, the bar D24 is displayed in an overlapping manner. The bar D24 is displayed on the graph at a position corresponding to the captured time represented by the time parameter. For example, the bar D24 is a segment parallel to the vertical axis of the graph displayed on the screen D21 and is displayed such that a middle point of the segment is placed on the graph.

On the screen D23, images P included in the time lapse image TP are displayed to be aligned from the left side to the right side in order of the captured time. Here, the image P included in the time lapse image TP displayed on the screen D23 is displayed as an image in which a cell region in the reference region RS is illustrated. On the screen D23, the bar D25 is displayed in an overlapping manner. The bar D25 is displayed to overlap on the image P corresponding to the captured time represented by the time parameter.

When a user such as an observer selects a part of the graph displayed on the screen D21, the value of the time parameter is changed to the captured time corresponding to the selected part. In addition, when a user selects an image P that is displayed to be aligned on the screen D23, the value of the time parameter is changed to a captured time of the selected image P. A user may move the bar D24 on the graph displayed on the screen D21 using a mouse or a touch panel. In addition, the user may move the bar D25 on the time lapse image TP displayed on the screen D23. Such a user's selection operation is performed through a mouse or a touch panel of the operation unit 45.

When the value of the time parameter is changed, the image displayed on the screen D22 among the images P included in the time lapse image TP is immediately changed. In addition, when the value of the time parameter is changed, the position of the bar D24 on the graph displayed on the screen D21 and the position of the bar D25 displayed on the time lapse image TP displayed on the screen D23 are immediately changed.

The button D26 is a button used for performing operations of reproduction and reverse reproduction of a moving image of the time lapse image TP displayed on the screen D22.

In addition, the display control unit 427 may display the screen D2 based on the ratio of the area of the cell region in the reference region RS to the reference region RS instead of the area of the cell region in the reference region RS. In such a case, on the screen D21, a graph representing a change in the time series of the ratio of the area of the cell region within the reference region RS the reference region RS is displayed. The graph displayed on this screen D21, for example, is the graph as illustrated in FIG. 13. In addition, in this case, on the screen D22, an image P included in the time lapse image TP is displayed as a moving image in which an area other than the cell region in the reference region RS is illustrated. On the screen D23, the images P included in the time lapse image TP are displayed such that areas other than the cell region in the reference region RS are illustrated to be aligned.

Figure 18:
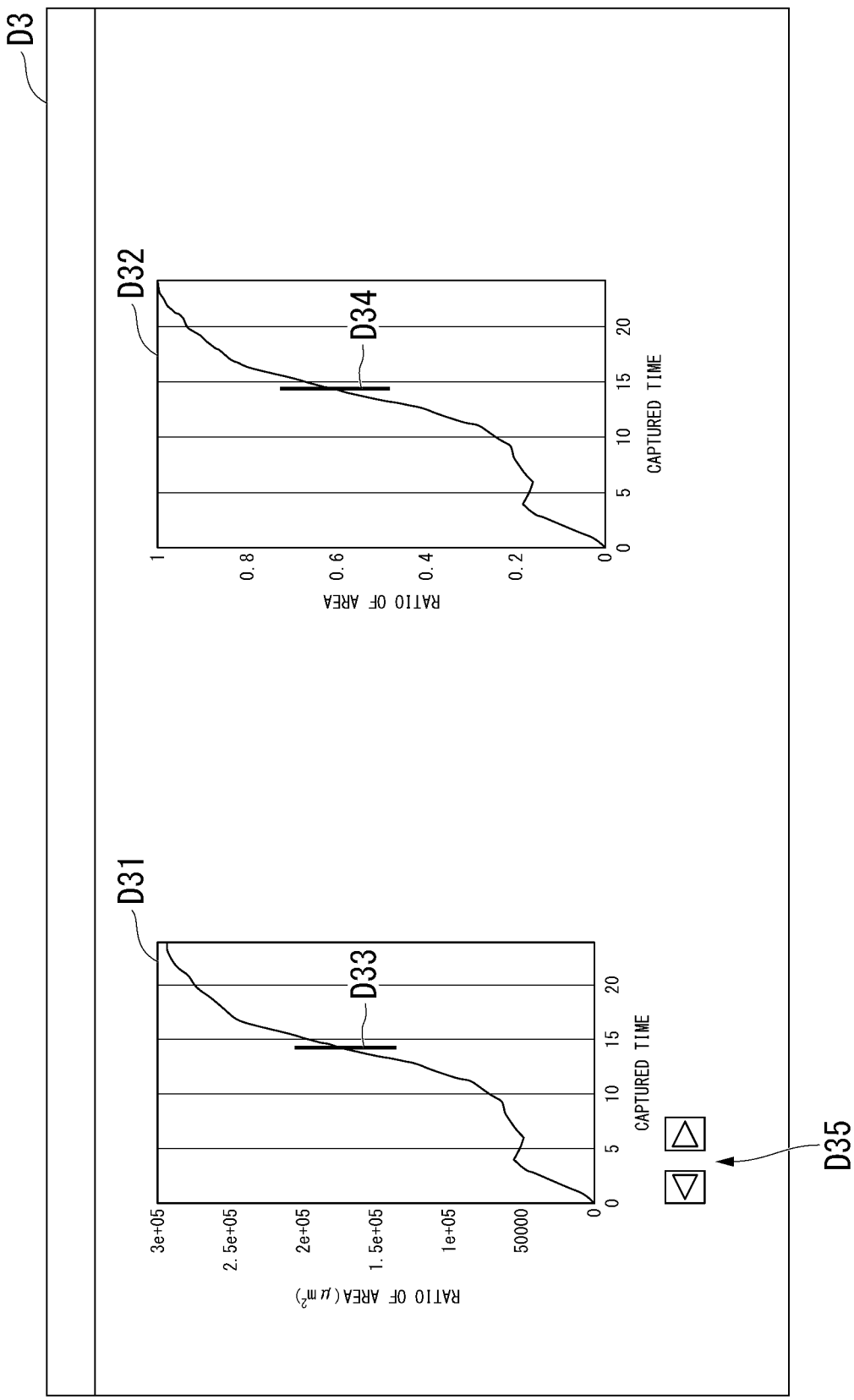
FIG. 18 is a diagram illustrating an example of a screen of a GUI according to the fourth embodiment.

FIG. 18 is a diagram illustrating an example of the screen D3 of the GUI according to this embodiment. The display control unit 427 displays the screen D3 based on the area of the cell region in the reference region RS and the ratio of the area of the cell region in the reference region RS to the reference region RS. The screen D3 is configured to include a screen D31, a screen D32, a bar D33, a bar D34, and a button D35 as a plurality of display fields.

On the screen D31, a graph representing a change in the time series of the area of a cell region within a reference region RS is displayed. For example, the graph displayed on this screen D31 is the graph as illustrated in FIG. 9.

On the screen D32, a graph representing a change in the time series of the ratio of the area of the cell region within the reference region RS is displayed. For example, the graph displayed on this screen D32 is the graph as illustrated in FIG. 13.

Functions of the bar D33, the bar D34, and the button D35 are similar to the functions of the bar D24 and the button D26 illustrated in FIG. 17, and thus description thereof will be omitted.

In addition, on the screen D32, a graph representing a change in the time series of a scratch area closure ratio may be displayed instead of the change in the time series of the ratio of the area of the cell region within the reference region RS to the reference region RS.

As described above, an image analyzer according to this embodiment (the arithmetic operation unit 42c according to this embodiment) includes a control unit (the display control unit 427 according to this embodiment). The control unit (the display control unit 427 according to this embodiment) causes the display device (the display unit 44 according to this embodiment) to display the change in the time series of the area of the cell region in the reference region RS of the image P calculated by the calculation unit 426 and/or the change in the time series of the ratio of the area of the cell region in the reference region RS of the image P to the reference region RS calculated by the area ratio calculating unit 429a.

By employing this configuration, the image analyzer according to this embodiment can display the change in the time series of the area of the cell region within the scratch area and thus can visualize the migration ability of cells.

In addition, in each of the embodiments described above, although an example of a case in which the image analyzer is realized as each of the arithmetic operation unit 42, the arithmetic operation unit 42a, the arithmetic operation unit 42b, and the arithmetic operation unit 42c of the control device 41 included in the incubator 11 has been described, the configuration is not limited thereto. The image analyzer may be a unit that is separate from the incubator 11. In a case in which the image analyzer is a unit that is separate from the incubator 11, the image analyzer acquires a time lapse image TP from an external device and analyzes the acquired time lapse image.

In a case in which the image analyzer acquires a time lapse image TP from an external device and analyzes the acquired time lapse image, the image analyzer, for example, is a server of cloud computing that analyzes the time lapse image TP. In addition, the external device, for example, is a terminal device. In this case, a data processing system including the image analyzer and the external device is provided.

Then, by starting the operation of a web browser in a terminal device (user's terminal) and operating a GUI on the web browser, a user uploads the time lapse image TP to the image analyzer that is a server together with identification information (an identification number or the like of the user or the terminal) through the Internet. The image analyzer performs the image analysis process and the migration ability evaluating process according to each of the embodiments described above based on the uploaded time lapse image TP. The image analyzer outputs analysis results (the analysis information described above) of the image analysis process and the migration ability evaluating process to the terminal device together with the identification information (an identification number or the like of the user or the terminal).

The terminal device displays the analysis results (the analysis information described above) that have been output from the image analyzer, which is a server, and have been received on a display (for example, the display unit 44). The terminal device may display the analysis results under the control of the display control unit 427 of the image analyzer, or the terminal device may include a display control unit having the same function as the display control unit 427 and display the analysis results using this display control unit. For example, the terminal device display analysis results using the screen D1, the screen D2, or the screen D3 according to the fourth embodiment described above. For example, a data processing system outputting the analysis information to a user's terminal using cloud computing includes the image analyzer as a server, and the server includes: an acquisition unit (the image acquiring unit 420) that acquires a time lapse image TP of cells through a network; an area setting unit 425 that sets a scratch area formed in a culture area of cells from a reference image PS of the time lapse image TP as a reference region RS; a calculation unit 426 that calculates an area of each cell region of cells within the reference region RS from the time lapse image TP and generates the analysis information described above displayed in a web browser in a terminal of a user based on the calculated area; and a control unit (for example, the display control unit 427) that outputs the analysis information to the terminal of the user. In addition, the server (for example, the image analyzer) may include an operation unit (an input unit) to which a user can input information such as the operation unit 45 described above.

As described above, the image analyzer includes: an area setting unit that extracts a scratch area that is an area in which having no cells from a reference image selected from a plurality of images acquired by imaging cells in a time series and sets a reference region corresponding to the scratch area in the plurality of images; a calculation unit that calculates an area of a cell region within the reference region and/or the ratio of the area of the cell region to the reference region from the plurality of images; and a control unit that causes a display device to display a change in the time series of the calculated area of the cell region and/or the ratio of the area of the cell region.

As described above, the image analyzer includes a storage unit that stores a program executed by the image analyzer and a control unit that controls an operation of the image analyzer by executing the program. The control unit selects a reference image from a plurality of images acquired by imaging cells in a time series, extracts an area having no cells in the reference image as a scratch area, sets a reference region corresponding to the scratch area in each of the plurality of images, sets a predetermined color for a cell region positioned within the reference region of each of the plurality of images, and controls an operation of outputting a change in the time series of the cell region to the display device.

A part of the image analyzer (for example, the arithmetic operation unit 42, the arithmetic operation unit 42a, the arithmetic operation unit 42b, or the arithmetic operation unit 42c) according to the embodiment described above, for example, the image acquiring unit 420, the image processing unit 421, the reference image selecting unit 422, the cell region determining unit 423, the scratch area extracting unit 424, the area setting unit 425, the calculation unit 426, the display control unit 427, the reference region area calculating unit 428a, the area ratio calculating unit 429a, and the migration ability evaluating unit 430b may be realized using a computer. In such a case, the part may be realized by recording a program for realizing this control function on a computer-readable recording medium and causing a computer system to read and execute the program recorded on this recording medium. In addition, a "computer system" described here is a computer system built into the image analyzer (for example, the arithmetic operation unit 42, the arithmetic operation unit 42a, the arithmetic operation unit 42b, or the arithmetic operation unit 42c) and includes an OS and hardware such as peripherals. In addition, the "computer-readable recording medium" represents a portable medium such as a flexible disc, a magneto-optical disk, a ROM, or a CD-ROM or a storage device such as a hard disk built into a computer system. Furthermore, the "computer-readable recording medium" may include a medium dynamically storing the program for a short time such as a communication line of a case in which the program is transmitted through a network such as the Internet or a communication circuit line such as a telephone line and a medium storing the program for a predetermined time such as an internal volatile memory of the computer system that becomes a server or a client in such a case. In addition, the program described above may be a program used for realizing a part of the function described above or a program that can realize the function described above in combination with a program that is already recorded in the computer system.

Some or all of the image analyzer (for example, the arithmetic operation unit 42, the arithmetic operation unit 42a, the arithmetic operation unit 42b, or the arithmetic operation unit 42c) according to the embodiment described above may be realized as an integrated circuit such as a large-scale integration (LSI). Each functional block of the image analyzer (for example, the arithmetic operation unit 42, the arithmetic operation unit 42a, the arithmetic operation unit 42b, or the arithmetic operation unit 42c) may be individually configured as a processor, or some or all of the functional blocks may be integrated and configured as a processor. In addition, a technique used for configuring the integrated circuit is not limited to the LSI, and each function may be realized by a dedicated circuit or a general-purpose processor. Furthermore, in a case in which a technology of configuring an integrated circuit replacing the LSI emerges in accordance with the progress of semiconductor technologies, an integrated circuit using such a technology may be used.

As above, although the embodiment of the present invention has been described in detail with reference to the drawings, a specific configuration is not limited to that described above, and various design changes and the like can be made in a range not departing from the concept of the present invention.

REFERENCE SIGNS LIST

11 Incubator
42, 42a, 42b, 42c Arithmetic operation unit
422 Reference image selecting unit
423 Cell region determining unit
424 Scratch area extracting unit
426 Calculation unit
427 Display control unit
428a Reference region area calculating unit
429a Area ratio calculating unit
430b Migration ability evaluating unit
TP Time lapse image
P Image
PS Reference image
RS Reference region

The invention claimed is:

1. An image analyzer comprising:
a memory;
a central processing unit (CPU) connected to the memory and programmed to:
extract a scratch area, which is an area having no cells, from a reference image selected from a plurality of images acquired by imaging cells in a time series;
set, common to the plurality of images, a reference region corresponding to the scratch area in each of the plurality of images; and
control an operation of outputting to a display device a change in a time series of a cell region positioned within the reference region of each of the plurality of images,
wherein the CPU is programmed to extract the cell region for each of the acquired plurality of images in the time series by:
performing a filtering process on the acquired time series image so as to generate a filtered image;
generating a differential image by calculating, as pixel values of pixels of the differential image, absolute values of differences between (i) pixel values of pixels of the acquired time series image and (ii) pixel values of pixels of the filtered image;
performing a binarization process by comparing the pixel values of the pixels of the differential image to a predetermined threshold; and
smoothing a boundary on an image acquired by performing the binarization process on the differential image, the boundary being a boundary between the cell region and a region which is not the cell region.

2. The image analyzer according to claim 1, wherein the CPU is further programmed to calculate an area of the cell region within the reference region based on the cell region included in the plurality of images captured in the time series.

3. The image analyzer according to claim 2, wherein the CPU is further programmed to
calculate an area of the reference region; and
calculate a ratio of the area of the cell region within the reference region to the reference region based on the calculated area of the reference region and the calculated area of the cell region.

4. The image analyzer according to claim 1, wherein
the scratch area is extracted from the reference image based on luminance values of the reference image, and
the CPU is programmed to set the extracted scratch area as the reference region.

5. The image analyzer according to claim 1, wherein a scratch region, which is a gap formed in a culture area of cells, is extracted as the reference region from the reference image.

6. The image analyzer according to claim 1, wherein the CPU is further programmed to acquire operation information representing the reference region designated through an operation unit by a user in the reference image.

7. The image analyzer according to claim 2, wherein the CPU is further programmed to evaluate a migration ability of the cells based on a change in the time series of the calculated area of the cell region.

8. The image analyzer according to claim 1, wherein the CPU is further programmed to select the reference image from among the plurality of images captured in the time series.

9. A cell culture observation device comprising:
the image analyzer according to claim 1;
a culture device configured to culture the cells housed in a culture container; and
a microscope configured to capture the plurality of images.

10. An image analysis method comprising:
extracting a scratch area, which is an area having no cells, from a reference image selected from a plurality of images acquired by imaging cells in a time series;
setting, common to the plurality of images, a reference region corresponding to the scratch area in each of the plurality of images; and
outputting to a display device a change in a time series of a cell region positioned within the reference region of each of the plurality of images,
wherein the method further comprises extracting the cell region for each of the acquired plurality of images in the time series by:
performing a filtering process on the acquired time series image so as to generate a filtered image;
generating a differential image by calculating, as pixel values of pixels of the differential image, absolute values of differences between (i) pixel values of pixels of the acquired time series image and (ii) pixel values of pixels of the filtered image;
performing a binarization process by comparing the pixel values of the pixels of the differential image to a predetermined threshold; and
smoothing a boundary on an image acquired by performing the binarization process on the differential image, the boundary being a boundary between the cell region and a region which is not the cell region.

11. A non-transitory computer-readable medium storing instructions which, when executed by a computer, cause the computer to execute:
extracting a scratch area, which is an area having no cells, from a reference image selected from a plurality of images acquired by imaging cells in a time series;
setting, common to the plurality of images, a reference region corresponding to the scratch area in each of the plurality of images; and
outputting to a display device a change in a time series of a cell region positioned within the reference region of each of the plurality of images,
wherein the instructions further cause the computer to execute extracting the cell region for each of the acquired plurality of images in the time series by:
performing a filtering process on the acquired time series image so as to generate a filtered image;
generating a differential image by calculating, as pixel values of pixels of the differential image, absolute values of differences between (i) pixel values of pixels of the acquired time series image and (ii) pixel values of pixels of the filtered image;
performing a binarization process by comparing the pixel values of the pixels of the differential image to a predetermined threshold; and
smoothing a boundary on an image acquired by performing the binarization process on the differential image, the boundary being a boundary between the cell region and a region which is not the cell region.

12. A data processing system that outputs analysis information to a terminal of a user using cloud computing, the data processing system comprising a server that comprises:
an acquisition unit configured to acquire through a network a plurality of images acquired by imaging cells in a time series;
an area setting unit configured to
(i) extract a scratch area, which is an area having no cells, from a reference image selected from the plurality of images acquired by imaging cells in the time series and
(ii) set, common to the plurality of images, a reference region corresponding to the scratch area in each of the plurality of images; and
a control unit configured to control an operation of outputting to a display device of the terminal of the user a change in a time series of a cell region positioned within the reference region of each of the plurality of images,
wherein the control unit is further configured to extract the cell region for each of the acquired plurality of images in the time series by:
performing a filtering process on the acquired time series image so as to generate a filtered image;
generating a differential image by calculating, as pixel values of pixels of the differential image, absolute values of differences between (i) pixel values of pixels of the acquired time series image and (ii) pixel values of pixels of the filtered image;
performing a binarization process by comparing the pixel values of the pixels of the differential image to a predetermined threshold; and
smoothing a boundary on an image acquired by performing the binarization process on the differential image, the boundary being a boundary between the cell region and a region which is not the cell region.

* * * * *